(12) United States Patent
Ferreira Vila Real et al.

(10) Patent No.: US 9,919,021 B2
(45) Date of Patent: Mar. 20, 2018

(54) BRAIN PERMEANT PEPTIDOMIMETIC BETA-SECRETASE 1 INHIBITORS FOR THE TREATMENT OR PROPHYLAXIS OF NEUROLOGICAL DISORDERS OR CONDITIONS

(71) Applicant: IBET—INSTITUTO DE BIOLOGIA EXPERIMENTAL E TECNOLOGICA, Oeiras (PT)

(72) Inventors: Helder Joao Ferreira Vila Real, Queijas (PT); Ana Luisa Ferreira Simplicio, Sao Domingos De Rana (PT); Olga Iranzo Casanova, Marseilles (FR); Christopher David Maycock, Parede (PT)

(73) Assignee: IBET—INSTITUTO DE BIOLOGIA EXPERIMENTAL E TECNOLÓGICA, Oeiras (PT)

( * ) Notice: Subject to any disclaimer, the term of this patent is extended or adjusted under 35 U.S.C. 154(b) by 0 days.

(21) Appl. No.: 15/099,860

(22) Filed: Apr. 15, 2016

(65) Prior Publication Data

US 2017/0296618 A1 Oct. 19, 2017

(51) Int. Cl.
*A61K 38/08* (2006.01)
(52) U.S. Cl.
CPC .................. *A61K 38/08* (2013.01)
(58) Field of Classification Search
None
See application file for complete search history.

(56) References Cited

U.S. PATENT DOCUMENTS

2008/0112946 A1* 5/2008 Koelsch ............... C07K 1/1136
424/94.66

OTHER PUBLICATIONS

Ghosh 2000 "design of potent inhibitors for human brain memapsin 2" j am chem soc 122:3522-3523.*
Ghosh 2012 "developing b-secratase inhibitors for treatment of alzheimer's disease" j neurochem 120(suppl):71-83.*
Medicinenet 2017 "medical definition of prophylactic" accessed from medicinenet.com.*
Reitz 2016 "toward precision medicine in alzheimer's disease" ann trans med 4(6):107.*
Stanford 2016 "alzheimer's prevention, treatment and research" accessed from stanfordhealthcare.org.*
Z. Zoira, et al; Small-sized BACE1 inhibitors; Drugs of the Future; 2006; vol. 31; No. 1; pp. 53-63.
N. J. Abbott, et al; Structure and function of the blood-brain barrier; Neurobiology of Disease; 2010; vol. 37; pp. 13-25.
H. Sharma, et al; International Review of Neurobiology; 2012; vol. 102; pp. 61-62.
S. J. Stachel; Progress toward the development of a viable BACE-1 inhibitor; Drug Development Research; 2009; vol. 70; pp. 101-110.
I. T. Ivanov, et al; New peptide mimetics with potential . . . ; Bulgarian Chemical Communications; 2009; vol. 41; No. 2; pp. 143-148.
R. T. Turner III; et al; Subsite specificity of memapsin 2 . . . ; Biochemistry; 2001; vol. 40; No. 34; pp. 10001-10006.
I. Brasnjevic, et al; Delivery of peptide and protein drugs over the blood-brain barrier; Progress in Neurobiology; 2009; vol. 87; pp. 212-251.
E. Gospodarska, et al; Binding studies of truncated variants of the . . . ; Biochimica et Biophysica Acta; 2011; pp. 592-609.

* cited by examiner

*Primary Examiner* — Adam Weidner
(74) *Attorney, Agent, or Firm* — HM Law Group LLP; Vani Moodley, Esq.

(57) ABSTRACT

The present application presents novel peptidomimetic substituted hydroxyethylene compounds, which are inhibitors of beta amyloid cleavage enzyme, capable to permeate the brain and to achieve therapeutic concentrations in the target organ, the brain. These compounds are incorporated in pharmaceutical compositions and applied in the treatment or prophylaxis of neurological disorders or conditions and also other disorders or conditions including Down's syndrome and diabetes.

17 Claims, 7 Drawing Sheets

BRAIN PERMEANT PEPTIDOMIMETIC BETA-SECRETASE 1 INHIBITORS FOR THE TREATMENT OR PROPHYLAXIS OF NEUROLOGICAL DISORDERS OR CONDITIONS

TECHNICAL FIELD

The present application relates to peptidomimetic substituted hydroxyethylene compounds, which are inhibitors of beta amyloid cleavage enzyme, capable to permeate the brain and to achieve therapeutic concentrations in the target organ, the brain. These compounds are incorporated in pharmaceutical compositions and applied in the treatment or prophylaxis of neurological disorders or conditions and also other disorders or conditions including Down's syndrome and diabetes.

BACKGROUND

Alzheimer's disease (AD) is a progressive neurodegenerative disease of the central nervous system and the most common form of irreversible dementia. It is generally characterized by a slow but inflexible progression of dementia, associated with cognitive and memory decline, speech loss and personality changes. The memory loss is characteristic of AD, firstly a gradual loss of short-period memory occurs, which ultimately is extended to the more consolidated memory.

The prodromal phase of AD is characterized by the appearance of cognitive deficits, depression and functional impairment, while in the early stage of AD a mild cognitive impairment emerges.

Two kinds of hallmark pathological lesions occur, consisting on both amyloid plaques and neurofibrillary tangles in the brain memory and cognition regions.

Amyloid beta peptide (Aβ), a highly insoluble peptide with high tendency to oligomerize and aggregate, is the primary component of the amyloid plaques. The formation of Aβ occurs due to the sequential cleavage of the amyloid precursor protein by β-secretase and γ-secretase. From the proteolytic fragmentation of amyloid precursor protein (APP), several isoforms of Aβ peptide are released, among which Aβ$_{42}$, a very low soluble isoform forty two amino acid long.

Neurofibrillary tangles are formed by the accumulation of abnormal filaments of tau protein. Tau is a soluble microtubule-binding protein, which supports axonal transport and cytoskeleton growth, by stabilizing microtubules and promoting tubulin assembly into microtubules. Hyperphosphorylation of tau proteins in AD causes the detachment of tau proteins from the microtubule. The soluble tau proteins may then aggregate into soluble tau aggregates and insoluble paired helical filaments that ultimately end in the formation of neurofibrillary tangles. This microtubule destabilization caused by direct toxic effects of both soluble hyperphosphorylated tau and fibrillar tau leads to axonal transport impairment causing a progressive loss of neurons. Aβ was referred to cause hyperphosphorylation of tau proteins turning it responsible for neurofibrillary tangles occurrence.

The excessive production of Aβ in the human body causes its accumulation and deposition contributing to the pathological development of the disease that not only occurs in AD but also in other diseases.

Accumulation of Aβ42 in the spinal cord motor neurons plays a role in the pathogenesis of neurodegeneration in Amyotrophic lateral sclerosis.

The most common form of cerebral amyloid angiopathy worldwide is associated with fibrillar amyloid deposition of Aβ in brain blood vessels. In addition, cerebral amyloid angiopathy is itself a risk factor for the development of cerebral ischemia.

Hereditary cerebral haemorrhage with amyloidosis of the Dutch-type is an autosomal dominant hereditary disease in the amyloid precursor protein gene leading to altered Aβ cleavage and secretion resulting in Aβ accumulation in cerebral vessels, leading to haemorrhages and infarcts.

Abnormal accumulations of Aβ in human muscle found by Askanas et al., 1992 in inclusion body myositis patients emphasises the role of Aβ in the pathogenesis of diseases outside the central nervous system defined as peripheral amyloidoses.

More than 70% of familial Creutzfeldt-Jakob's disease, a prion disorder, possesses an E200K mutation, a nonconservative substitution of lysine for glutamate at codon 200, which has been described to increase Aβ deposition, supporting the idea of cooperative interaction with prion protein to result in disease.

The development of Alzheimer's disease by Down's syndrome patients at the age of 40 years is associated with the accumulation of deposits of Aβ due to an overexpression of amyloid precursor protein. In addition, Parkinson's disease (PD)-related dementia was also found to be associated with AD-pathology.

Head trauma, acquired immunodeficiency syndrome and stroke may play an important role in the pathogenesis of Alzheimer's disease since the deposition of Aβ has been observed in patients suffering severe head trauma and in HIV positive patients, also, patients that suffered acute ischemic stroke showed increased levels of circulating Aβ.

Agents lowering the production of Aβ, through the inhibition of β- or γ-secretase may block or delay AD progression and also other diseases, where excessive production of Aβ in the human body may lead to Aβ accumulation and deposition.

Particularly, pharmaceutical agents designed to inhibit β-secretase should decrease Aβ levels and consequently reduce the occurrence of amyloid plaques and neurofibrillary tangles.

Peptidomimetic β-secretase 1 inhibitors have shown to be ineffective in the treatment of Alzheimer's disease, despite their in vitro high potency inhibition of β-secretase 1. This kind of inhibitors lacks the required pharmacokinetic properties to cross the Blood-Brain Barrier (BBB). Their large size and high hydrophilicity were pointed as the main factor limiting the BBB crossing by diffusion.

Peptidomimetics are compounds whose pharmacophore mimics a natural protein or peptide by retaining their capacity to interact with a specific biological target.

OM00-3, was developed, which is one of the most potent ever reported BACE-1 inhibitors. This inhibitor is composed of natural amino acids plus an isostere moiety, a hydroxyethylene Leucine-Alanine dipeptide transition-state isostere, furnishing a non-cleavable carbon-carbon linkage for BACE-1 inhibition. OM00-3 has been optimized for the inhibition of BACE-1 for which the preference index of each amino acid has been reported. However OM00-3 is not permeable through the BBB due to his large size and hydrophilicity.

Progress led to the development of non-peptidic inhibitors. Despite being much smaller and hydrophobic in relation to peptidomimetic inhibitors, which are good properties to allow permeation through the BBB, efflux by P-glycoprotein has been reported, which limits the achievement of clinically relevant concentrations in the central nervous system. Also their small size contributes to increased toxicity due to nonspecificity.

BACE-1 inhibitors may also inhibit beta-secretase 2 (BACE-2), which has high homology with BACE-1, but is particularly important to avoid its inhibition since it may favour AD. On the other hand BACE-2 inhibitors may be used to induce expansion of functional pancreatic β cell mass for the treatment of type 2 diabetes.

Presently there is no effective treatment capable of modifying the progression of Alzheimer's disease. Currently available drugs only act on symptomatic improvement, while the development of drugs capable of blocking or delaying the disease progression remains a challenging unmet need, mainly due to β-secretase 1 inhibitors limitation in crossing the BBB.

A vascular theory for the development of Alzheimer's disease claims that a substantial amount of Aβ peptide in the brain of Alzheimer's disease patients is originated in the systemic circulation. In addition it was found that Aβ peptide transport across the BBB is mediated through transcytosis by interaction with the receptor for advanced glycation end products (RAGE). Transcytosis is a mechanism allowing the mediation of macromolecules transport from one side of a biological membrane onto the other side, by means of intracellular vesicles formation. In line with this, a binding region was identified in the Aβ peptide, responsible for its recognition by RAGE. This is a seven amino acid fragment of residues consisting on the amino acid sequence between residue number seventeen to the twenty third of Aβ peptide: LVFFAED [Aβ (17-23)] (SEQ ID No: 1). This sequence has also been proved to competitively inhibit the entrance of Aβ peptide into cells expressing RAGE. Also it was concluded that a sequence to recognize RAGE should have a highly hydrophobic segment flanked by two negatively charged residues at the C terminus Aβ (17-23).

In summary, there is yet a need for a strategy with an effective delivery of a BACE-1 inhibitor to the target organ, the brain. The present application comprises a specific drug design that simultaneously inhibits β-secretase 1 and also promotes brain permeation and the achievement of therapeutic concentrations in the brain, through the conjugation and/or combination of peptidomimetic β-secretase 1 inhibitors with an Aβ (17-23) ligand, known to bind RAGE receptor.

SUMMARY OF THE INVENTION

The present application discloses β-secretase 1 inhibitor compounds of the general formula I:

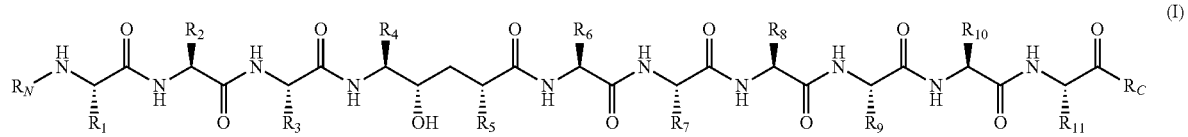

in which:
$R_1$ represents —H, —CH$_2$CH$_2$SCH$_3$, —CH$_2$CONH$_2$, —CH$_2$CH$_2$CONH$_2$, —CH$_2$COO$^-$ or —CH$_2$CH$_2$COO$^-$;
$R_2$ represents —CH(CH$_3$)$_2$, —CH$_2$CH(CH$_3$)$_2$, (1S)—CH(CH$_3$)CH$_2$CH$_3$, —CH$_2$-(4-(1H-imidazol-3-ium)) or —CH$_2$CH$_2$COO$^-$;

$R_3$ represents —CH$_3$, —CH$_2$CH(CH$_3$)$_2$, —CH$_2$-phenyl, —CH$_2$-phenol, —CH$_2$CH$_2$SCH$_3$, —CH$_2$OH, —CH$_2$CONH$_2$, —CH$_2$COO$^-$ or —CH$_2$CH$_2$COO$^-$;
$R_4$ represents —CH$_2$CH(CH$_3$)$_2$, —CH$_2$-phenyl, —CH$_2$-phenol or —CH$_2$CH$_2$SCH$_3$;
$R_5$ represents —CH$_3$;
$R_6$ represents —CH$_3$, —CH(CH$_3$)$_2$, —CH$_2$CH(CH$_3$)$_2$ or (1S)—CH(CH$_3$)CH$_2$CH$_3$;
$R_7$ and $R_8$ are independently selected from —CH$_2$-phenyl, —CH$_2$-phenol or —CH$_2$-(3-indole);
$R_9$ represents —H, —CH$_3$, —CH(CH$_3$)$_2$, —CH$_2$CH(CH$_3$)$_2$, (1S)—CH(CH$_3$)CH$_2$CH$_3$ or —CH$_2$CH$_2$*CH$_2$, wherein the *CH$_2$ is bonded to the adjacent NH to form a five membered heterocycle;
$R_{10}$ and $R_{11}$ are independently selected from —CH$_2$COO$^-$ or —CH$_2$CH$_2$COO$^-$;
$R_N$ represents —H or —COCH$_3$;
$R_C$ represents —NH$_2$ or —OH, and their enantiomers, diastereomers, tautomers, or pharmaceutically acceptable salts, solvates, protonated forms or deprotonated forms thereof.

In one embodiment, the compounds are of formula Ia to Ip, presented further ahead.

The present application also discloses a process for the preparation of the compounds described comprising the following steps:
a standard Solid Phase Peptide Synthesis using a Rink amide resin comprising at least 10 cycles of Fmoc deprotection and amino acids coupling, for the preparation of compounds with a amide in the C-terminal;
or a standard Solid Phase Peptide Synthesis using either Fmoc-Asp or Fmoc-Glu, both linked to a Wang resin, comprising at least 9 cycles of Fmoc deprotection and amino acids coupling, for the preparation of compounds with a carboxylic acid in the C-terminal;
optionally, a capping step with acetic anhydride, after Fmoc deprotection of the last added amino acid;
and deprotection of the amino acids lateral chains and resin cleavage.

In one embodiment, each cycle of the solid phase peptide synthesis for the preparation of compounds with a amide in the C-terminal, comprises two Fmoc deprotections, washing step, a single coupling with N,N,N',N'-Tetramethyl-O-(1H-benzotriazol-1-yl)uronium hexafluorophosphate (HBTU) activated amino acid and an additional washing.

In another embodiment, the Fmoc-protected amino acids are sequential added according to the following cycles:
the first cycle comprises the incorporation of: Fmoc-Asp(OtBu)-OH or Fmoc-Glu(OtBu)-OH;
the second cycle comprises the incorporation of: Fmoc-Asp(OtBu)-OH or Fmoc-Glu(OtBu)-OH;
the third cycle comprises the incorporation of: Fmoc-Gly-OH, Fmoc-Ala-OH, Fmoc-Val-OH, Fmoc-Leu-OH, Fmoc-Ile-OH or Fmoc-Pro-OH;
the fourth cycle comprises the incorporation of: Fmoc-Phe-OH, Fmoc-Tyr(tBu)-OH or Fmoc-Trp(Boc)-OH;

the fifth cycle comprises the incorporation of: Fmoc-Phe-OH, Fmoc-Tyr(tBu)-OH or Fmoc-Trp(Boc)-OH;

the sixth cycle comprises the incorporation of: Fmoc-Ala-OH, Fmoc-Val-OH, Fmoc-Leu-OH or Fmoc-Ile-OH;

the seventh cycle comprises the incorporation of an synthetic Fmoc-dipeptide hydroxyethylene isostere;

the eighth cycle is incorporated: Fmoc-Ala-OH, Fmoc-Leu-OH, Fmoc-Phe-OH, Fmoc-Tyr(tBu)-OH, Fmoc-Met-OH, Fmoc-Ser(tBu)-OH, Fmoc-Asn(Trt)-OH, Fmoc-Asp(OtBu)-OH or Fmoc-Glu(OtBu)-OH;

the ninth cycle comprises the incorporation of: Fmoc-Val-OH, Fmoc-Leu-OH, Fmoc-Ile-OH, Fmoc-His(Trt)-OH or Fmoc-Glu(OtBu)-OH;

and the tenth cycle comprises the incorporation of: Fmoc-Gly-OH, Fmoc-Met-OH, Fmoc-Asn(Trt)-OH, Fmoc-Gln(Trt)-OH, Fmoc-Asp(OtBu)-OH or Fmoc-Glu(OtBu)-OH.

In a further embodiment, the synthetic Fmoc-dipeptide hydroxyethylene isostere is synthesized following the steps:

convertion of Boc-L-leucine, Boc-L-phenylalanine, Boc-O-2-chlorotrityl-L-tyrosine or Boc-L-methionine into a Weinreb amide by treatment with N,O-dimethylhydroxyamine hydrochloride, 4-methylmorpholine and 1-ethyl-3-(3-dimethylaminopropyl)carbodiimide (EDC);

Weinreb amide reduction with LiAlH$_4$, followed by alkylation with lithium benzyl propargyl ether rendering an alkyne;

alkyne catalytic hydrogenation into a diol;

diol selective oxidation with bis(acetoxy)iodobenzene (BAIB) and (2,2,6,6-Tetramethylpiperidin-1-yl)oxy (TEMPO) rendering a lactone;

lactone methylation after treatment with lithium diisopropylamide (LDA) and MeI rendering a methyl-lactone;

methyl-lactone ring opening with aqueous lithium hydroxide and selective silylation of the free hydroxyl group with tert-butyldimethylsilyl chloride (TBDMSCl) and imidazole rendering an acid;

and acid tert-Butoxycarbonyl exchange by a fluorenylmethyloxycarbonyl protecting group after treatment with trifluoroacetic acid followed by Fmoc-succinimide in the presence of aqueous NaHCO$_3$, rendering a Fmoc-dipeptide hydroxyethylene isostere.

In another embodiment, each cycle of the solid phase peptide synthesis for the preparation of compounds with a carboxylic acid in the C-terminal, comprises two Fmoc deprotections, washing step, a single coupling with HBTU activated amino acid and an additional washing.

In one embodiment, the Fmoc-protected amino acids are sequential added according to the following cycles:

the first cycle comprises the incorporation of: Fmoc-Asp(OtBu)-OH or Fmoc-Glu(OtBu)-OH;

the second cycle comprises the incorporation of: Fmoc-Gly-OH, Fmoc-Ala-OH, Fmoc-Val-OH, Fmoc-Leu-OH, Fmoc-Ile-OH or Fmoc-Pro-OH;

the third cycle comprises the incorporation of: Fmoc-Phe-OH, Fmoc-Tyr(tBu)-OH or Fmoc-Trp(Boc)-OH;

the fourth cycle comprises the incorporation of: Fmoc-Phe-OH, Fmoc-Tyr(tBu)-OH or Fmoc-Trp(Boc)-OH;

the fifth cycle comprises the incorporation of: Fmoc-Ala-OH, Fmoc-Val-OH, Fmoc-Leu-OH or Fmoc-Ile-OH;

the sixth cycle comprises the incorporation of an synthetic Fmoc-dipeptide hydroxyethylene isostere;

the seventh cycle comprises the incorporation of: Fmoc-Ala-OH, Fmoc-Leu-OH, Fmoc-Phe-OH, Fmoc-Tyr(tBu)-OH, Fmoc-Met-OH, Fmoc-Ser(tBu)-OH, Fmoc-Asn(Trt)-OH, Fmoc-Asp(OtBu)-OH or Fmoc-Glu(OtBu)-OH;

the eighth cycle comprises the incorporation of: Fmoc-Val-OH, Fmoc-Leu-OH, Fmoc-Phe-OH, Fmoc-Ile-OH, Fmoc-His(Trt)-OH or Fmoc-Glu(OtBu)-OH;

and the ninth cycle comprises the incorporation of: Fmoc-Gly-OH, Fmoc-Met-OH, Fmoc-Asn(Trt)-OH, Fmoc-Gln(Trt)-OH, Fmoc-Asp(OtBu)-OH or Fmoc-Glu(OtBu)-OH.

In another embodiment, the synthetic Fmoc-dipeptide hydroxyethylene isostere is synthesized following the steps:

convertion of Boc-L-leucine, Boc-L-phenylalanine, Boc-O-2-chlorotrityl-L-tyrosine or Boc-L-methionine into a Weinreb amide by treatment with N,O-dimethylhydroxyamine hydrochloride, 4-methylmorpholine and EDC;

Weinreb amide reduction with LiAlH$_4$, followed by alkylation with lithium benzyl propargyl ether rendering an alkyne;

alkyne catalytic hydrogenation into a diol;

diol selective oxidation with BAIB and TEMPO rendering a lactone;

lactone methylation after treatment with LDA and MeI rendering a methyl-lactone;

methyl-lactone ring opening with aqueous lithium hydroxide and selective silylation of the free hydroxyl group with TBDMSCl and imidazole rendering an acid;

and acid tert-Butoxycarbonyl exchange by a fluorenylmethyloxycarbonyl protecting group after treatment with trifluoroacetic acid followed by Fmoc-succinimide in the presence of aqueous NaHCO$_3$, rendering a Fmoc-dipeptide hydroxyethylene isostere.

The present application further discloses the use of the compounds in the treatment or prophylaxis of neurological disorders or conditions including Alzheimer's disease, amyotrophic lateral sclerosis, cerebral amyloid angiopathy, cerebral ischemia, Creutzfeldt-Jacob's disease, dementia, head trauma, hereditary cerebral haemorrhage with amyloidosis of the Dutch-type, inclusion body myositis and other peripheral amyloidoses, major depression, mild cognitive impairment, neurological complications of acquired immunodeficiency syndrome, Parkinson's disease, Prion disorder, stroke, and also disorders or conditions including Down's syndrome and diabetes in a mammal, including a human.

In another embodiment, the compounds are for use in the treatment or prophylaxis of neurological disorders or conditions including Alzheimer's disease, for helping to prevent or delay the onset of Alzheimer's disease, for the treatment of patients with mild cognitive impairment and preventing or delaying the onset of Alzheimer's disease in those who would progress from mild cognitive impairment to Alzheimer's disease in a mammal, including a human.

DETAILED DESCRIPTION OF THE INVENTION

The present application refers to peptidomimetic substituted hydroxyethylene compounds and pharmaceutical compositions thereof for the treatment of Alzheimer's disease and, more particularly, compounds capable of inhibiting β-secretase 1 with high the capacity to permeate brain and to achieve therapeutic concentrations in the brain.

The compounds described herein are represented by the general Formula I:

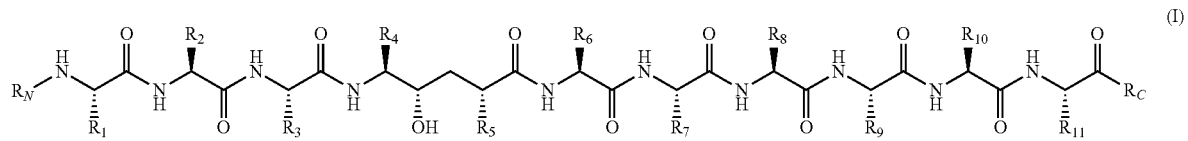

or enantiomers, diastereomers, tautomers, or pharmaceutically acceptable salts, solvates, protonated forms or deprotonated forms thereof,
wherein:

$R_1$ represents —H, —$CH_2CH_2SCH_3$, —$CH_2CONH_2$, —$CH_2CH_2CONH_2$, —$CH_2COO^-$ or —$CH_2CH_2COO^-$;

$R_2$ represents —$CH(CH_3)_2$, —$CH_2CH(CH_3)_2$, (1S)—$CH(CH_3)CH_2CH_3$, —$CH_2$-(4-(1H-imidazol-3-ium)) or —$CH_2CH_2COO^-$;

$R_3$ represents —$CH_3$, —$CH_2CH(CH_3)_2$, —$CH_2$-phenyl, —$CH_2$-phenol, —$CH_2CH_2SCH_3$, —$CH_2OH$, —$CH_2CONH_2$, —$CH_2COO^-$ or —$CH_2CH_2COO^-$;

$R_4$ represents —$CH_2CH(CH_3)_2$, —$CH_2$-phenyl, —$CH_2$-phenol or $CH_2CH_2SCH_3$;

$R_5$ represents —$CH_3$;

$R_6$ represents —$CH_3$, —$CH(CH_3)_2$, —$CH_2CH(CH_3)_2$ or (1S)—$CH(CH_3)CH_2CH_3$;

$R_7$ and $R_8$ are independently selected from —$CH_2$-phenyl, —$CH_2$-phenol or —$CH_2$-(3-indole);

$R_9$ represents —H, —$CH_3$, —$CH(CH_3)_2$, —$CH_2CH(CH_3)_2$, (1S)—$CH(CH_3)CH_2CH_3$ or —$CH_2CH_2*CH_2$, wherein the $*CH_2$ is bonded to the adjacent NH to form a five membered heterocycle;

$R_{10}$ and $R_{11}$ are independently selected from —$CH_2COO^-$ or —$CH_2CH_2COO^-$;

$R_N$ represents —H or —$COCH_3$;

$R_C$ represents —$NH_2$ or —OH.

In order to achieve clinically relevant concentrations of peptidomimetic β-secretase 1 inhibitors in the brain, the design of peptidomimetic β-secretase 1 inhibitors here described is based on the conjugation and/or combination of peptidomimetic β-secretase 1 inhibitors with an Aβ (17-23) ligand, known to bind RAGE receptor, in a way to contribute for the BBB permeation of peptidomimetic inhibitors.

To comprise both the effects of inhibiting β-secretase 1 and achieving clinically relevant concentrations in the brain after brain permeation, the design of the compounds of Formula I was based on the combination of the sequence APP (272-279) with Aβ (17-23), as described by FIG. 1. In addition a hydroxyethylene isostere is present between the residues with lateral chain $R_4$ and lateral chain $R_5$ of compounds of Formula I for BACE-1 inhibition.

To inhibit BACE-1 the molecular structure of compounds of Formula I was based on APP (272-279). The substituent groups of compounds of Formula I from $R_1$ to $R_8$ correspond to lateral chains of amino acids based on APP (272-279) as described in FIG. 1. These substituent groups were constricted according to the high preference index of β-secretase 1 for amino acids on each specific position [Turner et al., 2001].

According to the high preference index of β-secretase 1 for amino acids on each specific, it was established the following correspondence between substituent groups of compounds of Formula I from $R_1$ to $R_8$ to the lateral chains of the preferred amino acids:

$R_1$—E, Q, D, M, N and G;
$R_2$—I, V, L, E and H;
$R_3$—D, N, M, F, Y, L, E, S and A;
$R_4$—L, F, M and Y;
$R_5$—M, E, Q, A, D and S;
$R_6$—V, I, A, L, E, F, T, M, Y and S;
$R_7$—L, W, V, I, T, D, E, F, Y, M, K, R, A, G, S and Q;
$R_8$—D, E, W, Y, F, M, V, L, I, I, Q, A, G and S.

To allow RAGE receptor recognition, compounds of Formula I were designed based on Aβ (17-23). The substituent groups of compounds of Formula I from $R_5$ to $R_{11}$ correspond to lateral chains of amino acids based on Aβ (17-23) as described in FIG. 1. Concerning the properties of a ligand to recognize RAGE, the amino acid lateral chains: $R_5$, $R_6$, and $R_9$ are restricted to lateral chains of aliphatic hydrophobic amino acids, $R_7$ and $R_8$ are restricted to lateral chains of aromatic hydrophobic amino acids and $R_{10}$ and $R_{11}$ to lateral chains of negatively charged amino acids.

Aliphatic hydrophobic amino acids are: glycine (Gly), alanine (Ala), valine (Val), leucine (Leu), isoleucine (Ile) and proline (Pro).

Aromatic hydrophobic amino acids are: phenylalanine (Phe), tyrosine (Tyr) and tryptophan (Trp).

Negatively charged amino acids are: aspartic acid (Asp) and glutamic acid (Glu).

As described in FIG. 1 there is an overlay between the region of compounds of Formula I that inhibits β-secretase 1 and the region designed to recognize RAGE, consisting in the residues having the following lateral chains: $R_5$, $R_6$, $R_7$ and $R_8$. In this case these amino acid lateral chains were constricted to amino acids lateral chains simultaneously present in the high preference index of β-secretase 1 for amino acids in each specific position, as well as the kind of amino acid that RAGE needs for recognition on specific position.

The application also relates to a pharmaceutical composition comprising a compound of the Formula I, together with a pharmaceutically acceptable carrier or diluent.

The pharmaceutical composition herein described comprises an amount of a compound of the Formula I, that is effective in the treatment or prophylaxis of neurological disorders or conditions including Alzheimer's disease, amyotrophic lateral sclerosis, cerebral amyloid angiopathy, cerebral ischemia, Creutzfeldt-Jacob's disease, dementia, head trauma, hereditary cerebral haemorrhage with amyloidosis of the Dutch-type, inclusion body myositis and other peripheral amyloidoses, major depression, mild cognitive impairment, neurological complications of acquired immunodeficiency syndrome, Parkinson's disease, Prion disorder, stroke, and also disorders or conditions including Down's syndrome and diabetes in a mammal, including a human, together with a pharmaceutically acceptable carrier or diluent.

Additionally, the pharmaceutical composition herein described comprises an amount of a compound of the Formula I that is effective in the treatment or prophylaxis of neurological disorders or conditions including Alzheimer's disease, for helping to prevent or delay the onset of Alzheimer's disease, for the treatment of patients with mild cognitive impairment and preventing or delaying the onset of Alzheimer's disease in those who would progress from mild cognitive impairment to Alzheimer's disease in a mammal, including a human, together with a pharmaceutically acceptable carrier or diluent.

The pharmaceutical composition comprising an amount of a compound of the Formula I, together with a pharmaceutically acceptable carrier or diluent, is effective in the treatment or prophylaxis of Alzheimer's disease in a mammal, including a human.

This application relates to the use of a compound of the Formula I for the production of a medicament, together with a pharmaceutically acceptable carrier or diluent.

The term "treatment", as mentioned herein, refers to the act of reverting, alleviating, avoiding the progression or preventing the disorder or condition to which the term applies, or one or more of their symptoms.

The pharmaceutical compositions of the application comprise a particular embodiment an amount of a compound selected from the Formula (Ia) through (Ip):

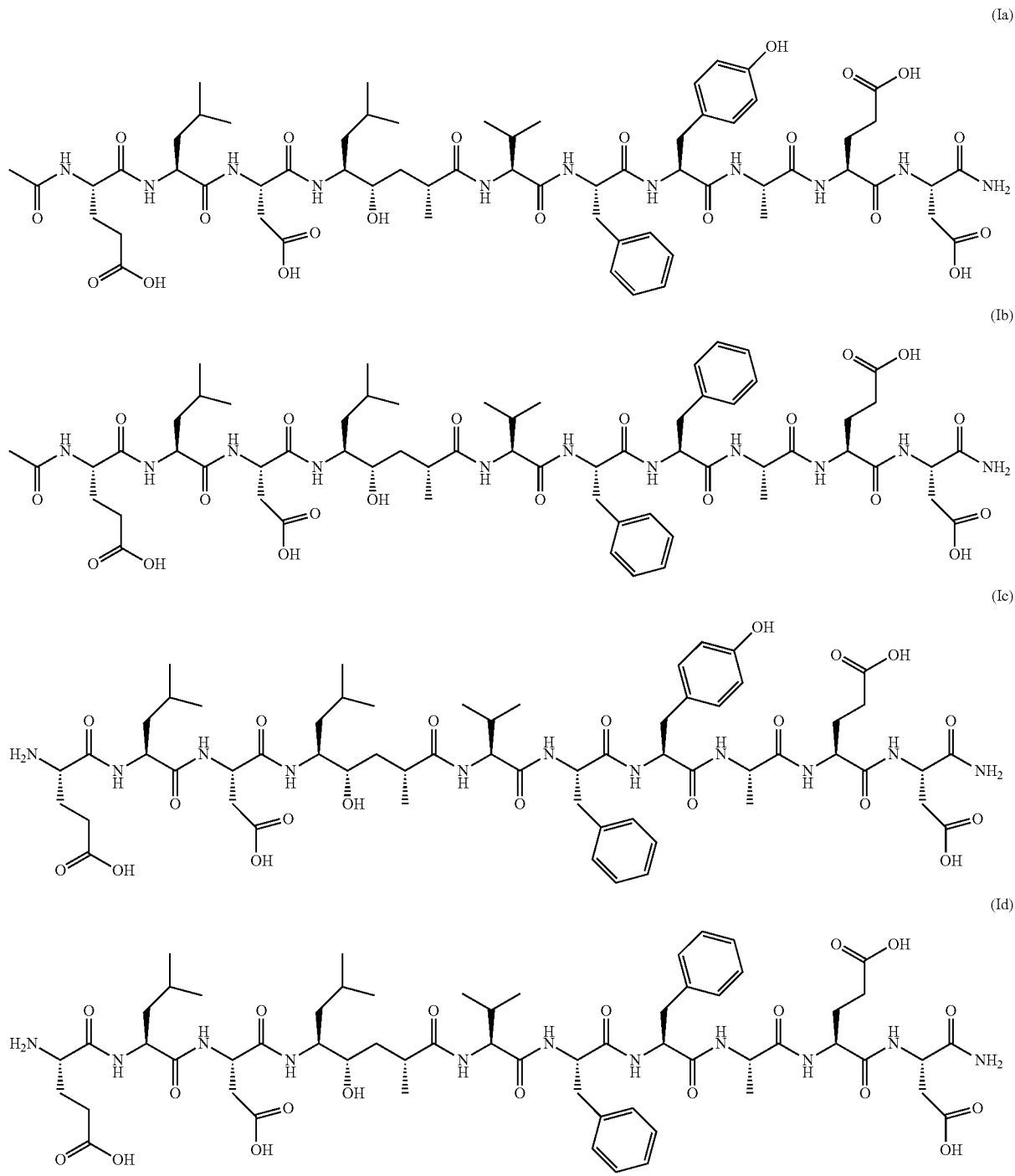

-continued
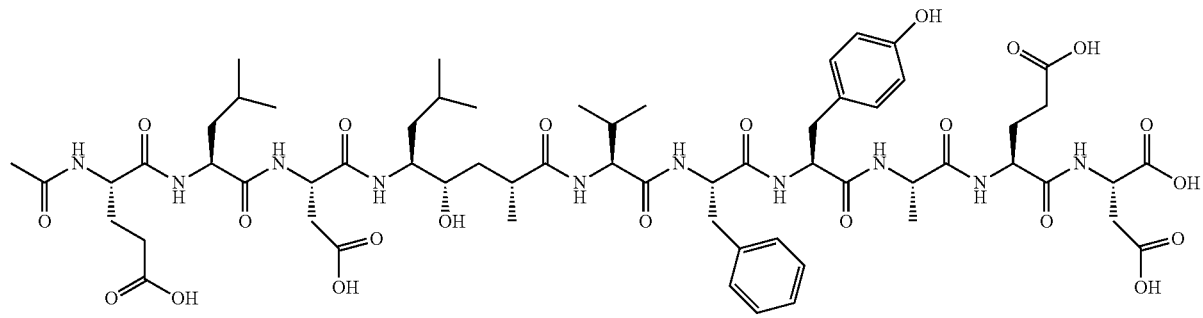
(Ie)
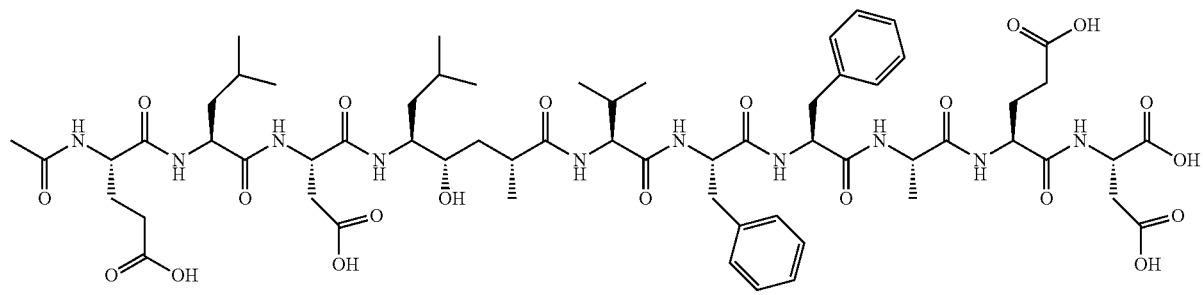
(If)
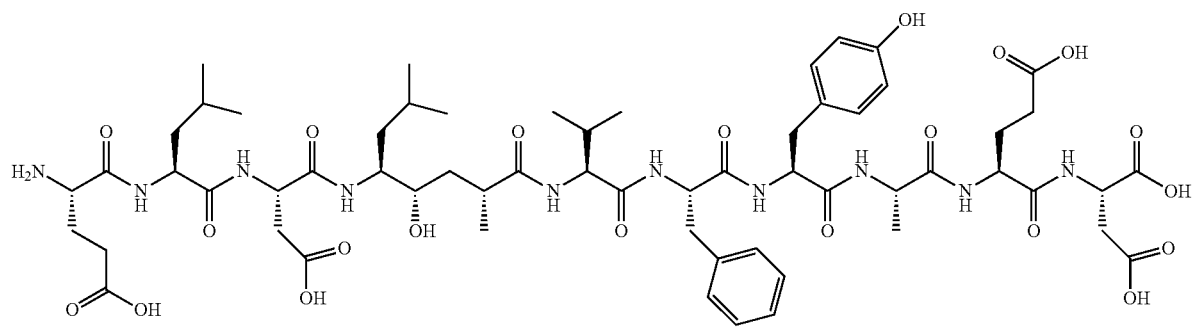
(Ig)
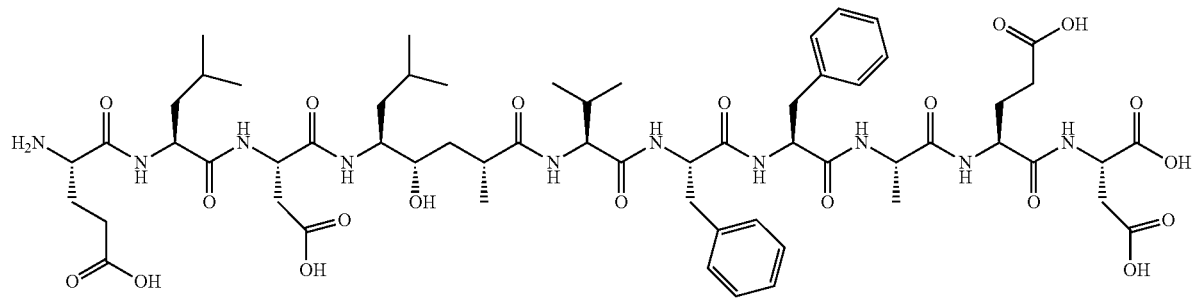
(Ih)

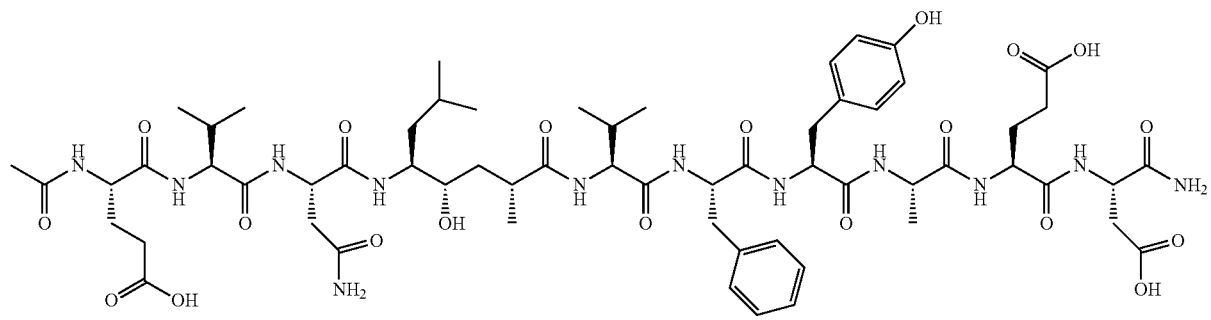
(Ii)
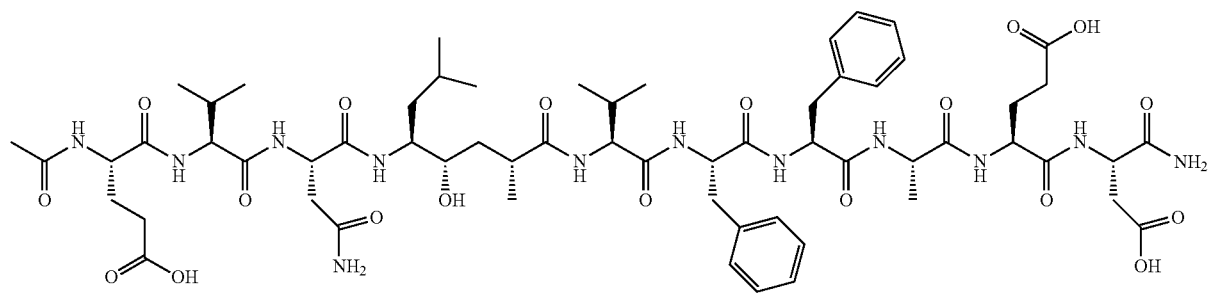
(Ij)
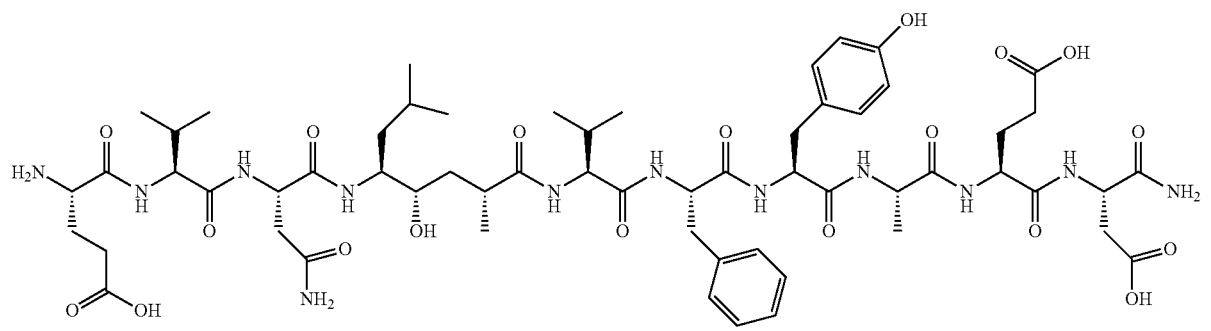
(Ik)
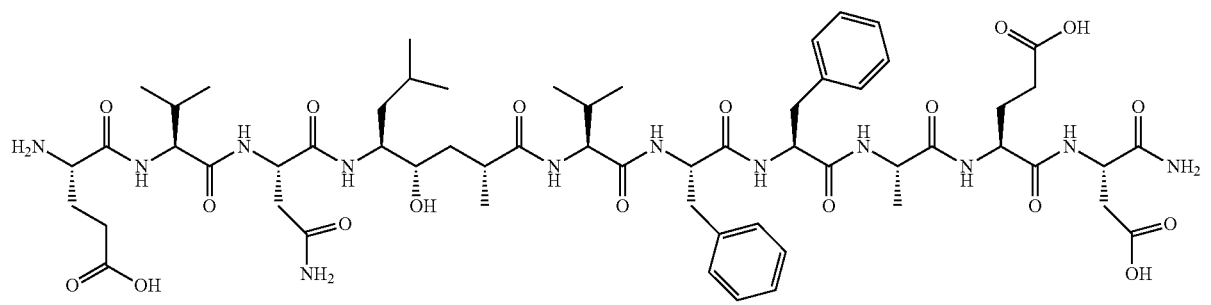
(Il)

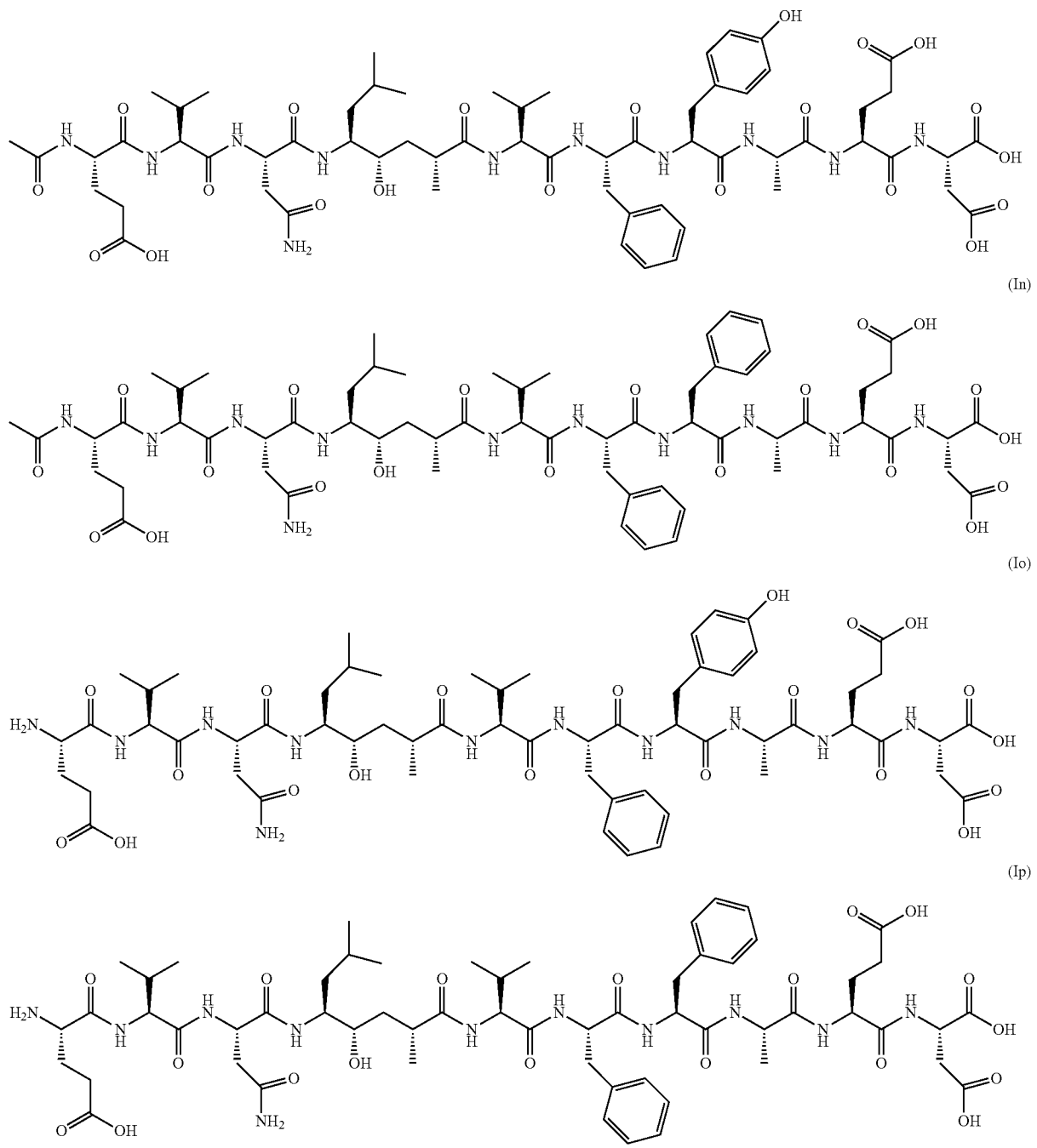

Compounds Ih and Ip correspond to the preferred amino acids combinations.

The acylation of the terminal amine as well as the amidation of the terminal carboxylic acid were included to remove terminal charges as well as to increase metabolic stability.

Compounds If, Id and Ib correspond respectively to compound Ih terminal amine acylation, terminal carboxylic amidation or both.

Compounds In, Il and Ij correspond respectively to compound Ip terminal amine acylation, terminal carboxylic amidation or both.

An advantage of having a tyrosine at position with lateral chain $R_8$ is to have a more specific inhibitor for β-secretase in relation to β-secretase 2, with inherently reduced potential to cause adverse effects.

Compounds: Ia, Ic, Ie, Ig, Ii, Ik, Im and Io correspond respectively to: Ib, Id, If, Ih, Ij, Il, In and Ip where the phenylalanine at position with lateral chain $R_8$ was exchanged for a tyrosine.

When compound Ia is administrated intravenous to mice it originates compound Ig which is an active metabolite found within therapeutic concentrations in the brains of mice even after the complete disappearance of compound Ia from the bloodstream (FIG. 5). This unexpected pharmacokinetic profile is related with the terminal charges generated by the metabolization of Ia into Ig. The increased hydrophilicity of compound Ig contributes to impede Ig clearance from the Central Nervous System into the bloodstream leading to a higher residence time in the brain since hydrophilic molecules have more difficulty to diffuse across the BBB.

Compound Ia is a prodrug of compound Ig and its unexpected metabolization is essential to achieve and maintain therapeutic concentrations of peptidomimetic β-secretase 1 inhibitors in the brain.

BRIEF DESCRIPTION OF DRAWINGS

Without intent to limit the disclosure herein, this application presents an attached drawing of illustrated embodiment for an easier understanding.

DESCRIPTION OF THE EMBODIMENTS

Figure 1:
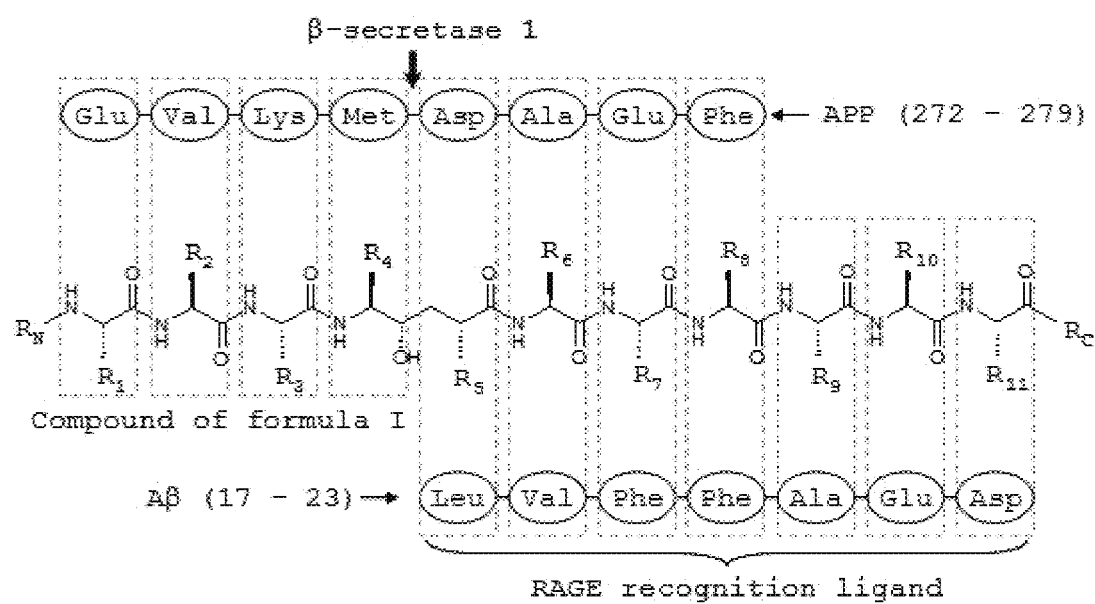
FIG. 1 illustrates the rational drug design of the compound of formula I, based on the APP (272-279) amino acid sequence that was merged with Aβ 17-23'.

The following optional embodiments are not intended to limit the scope of the present application.

The compound of formula IX is an amino and hydroxyl protected dipeptide hydroxyethylene isostere to be used in the synthesis of compound of formula I, and can be synthesized according to the procedure shown in Scheme 1 below.

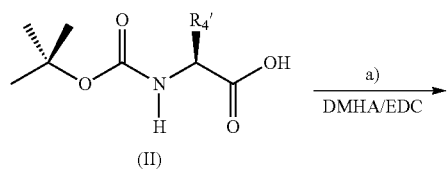

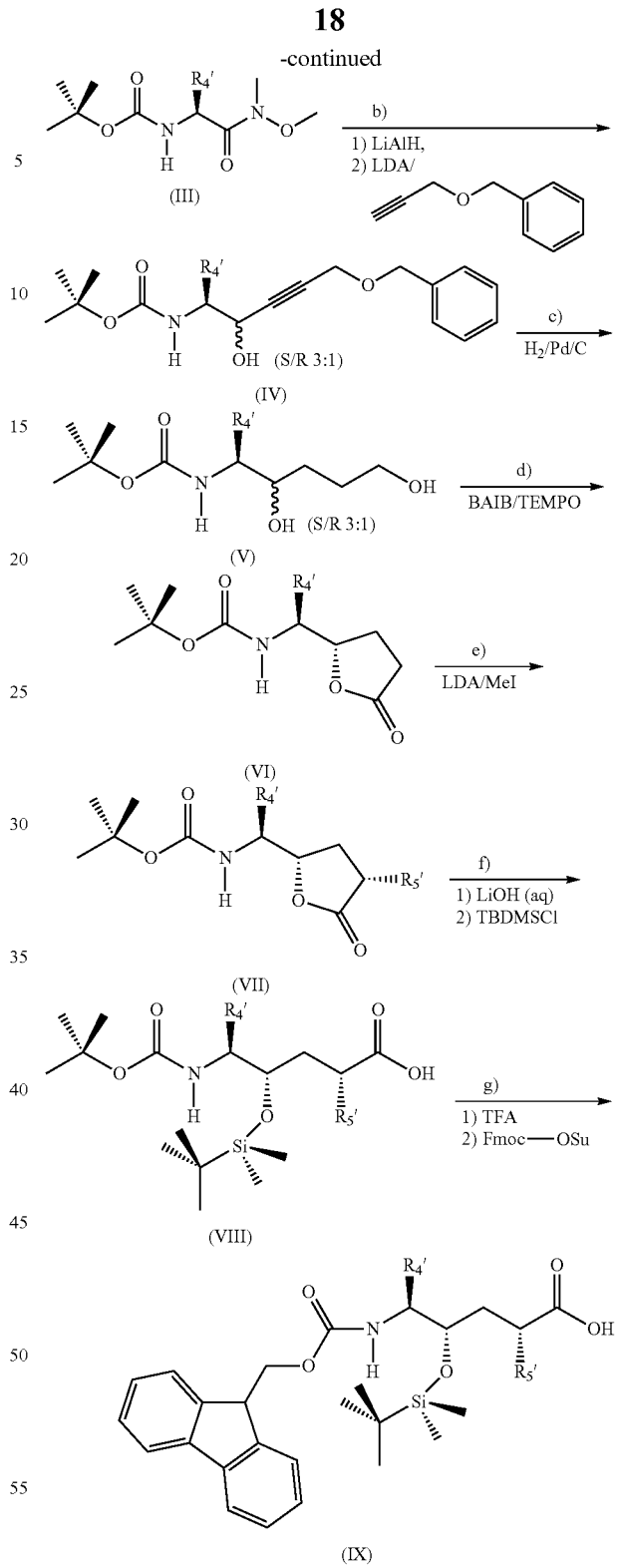

Referring to Scheme 1, the amino and hydroxyl protected dipeptide hydroxyethylene isostere, compound IX, is synthesized following the next chemical steps:

Step a): An amino acid (II): Boc-L-leucine, Boc-L-phenylalanine, Boc-O-2-chlorotrityl-L-tyrosine or Boc-L-methionine is converted into a Weinreb amide (III) by treatment with N,O-dimethylhydroxyamine hydrochloride, 4-methylmorpholine and EDC;

Step b): Weinreb amide reduction with LiAlH$_4$, followed by alkylation, without purification, with lithium benzyl propargyl ether rendering an alkyne (IV);

Step c): Alkyne (IV) catalytic hydrogenation into a diol (V);

Step d): Diol selective oxidation with BAIB and TEMPO rendering a lactone (VI), after which the diastereomeric mixture can be separated by liquid chromatography;

Step e): Lactone (VI) methylation after treatment with LDA and MeI rendering a methyl-lactone (VII);

Step f): Methyl-lactone ring opening with aqueous lithium hydroxide and selective silylation of the free hydroxyl group with TBDMSCl (VIII) and imidazole rendering an acid;

Step g): acid tert-Butoxycarbonyl exchange by a fluorenylmethyloxycarbonyl protecting group after treatment with trifluoroacetic acid followed by Fmoc-succinimide in the presence of aqueous NaHCO$_3$, rendering a Fmoc-dipeptide hydroxyethylene isostere (IX) suitable for peptide synthesis.

The produced alkyne (IV) in the step b) is a diastereomeric inseparable mixture, but the intended S-configuration is majority (75%).

This procedure of Scheme 1 is also fully described in the Example 1.

The compound of formula I can be synthesized by using a standard solid phase peptide synthesis procedure as illustrated in Scheme 2 below.

Scheme 2

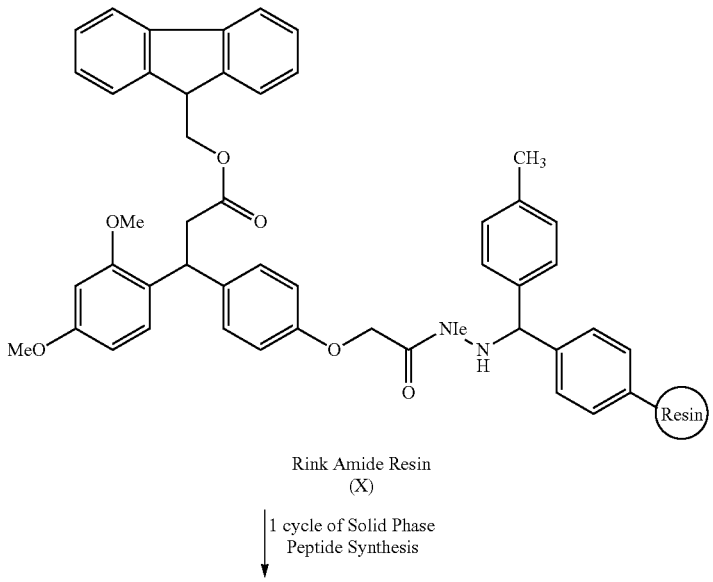

Rink Amide Resin
(X)

1 cycle of Solid Phase Peptide Synthesis

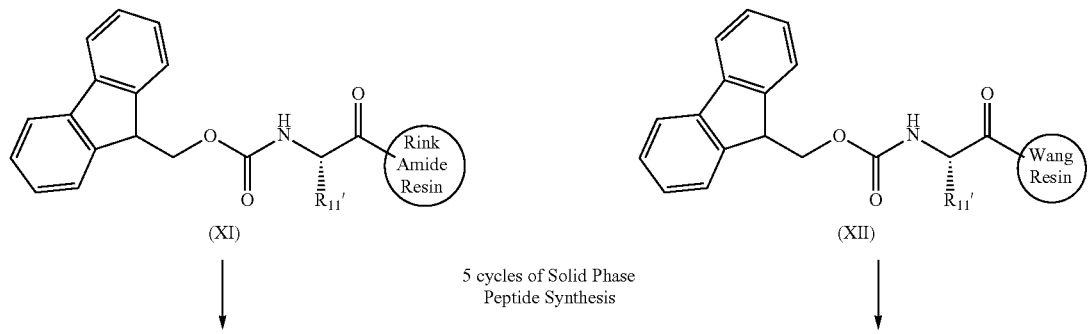

(XI)  (XII)

5 cycles of Solid Phase Peptide Synthesis

-continued
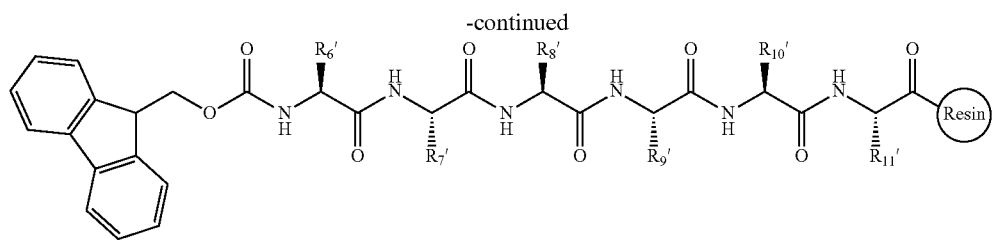
(XIII)
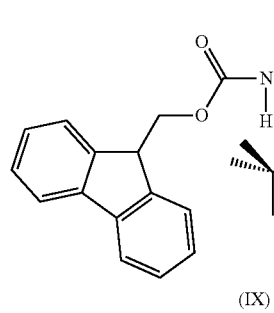
(IX)
1 cycle of Solid Phase Peptide Synthesis
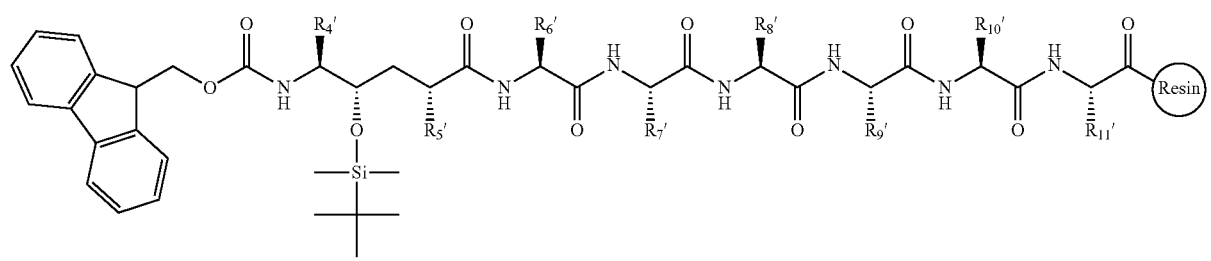
(XIV)
3 cycles of Solid Phase Peptide Synthesis
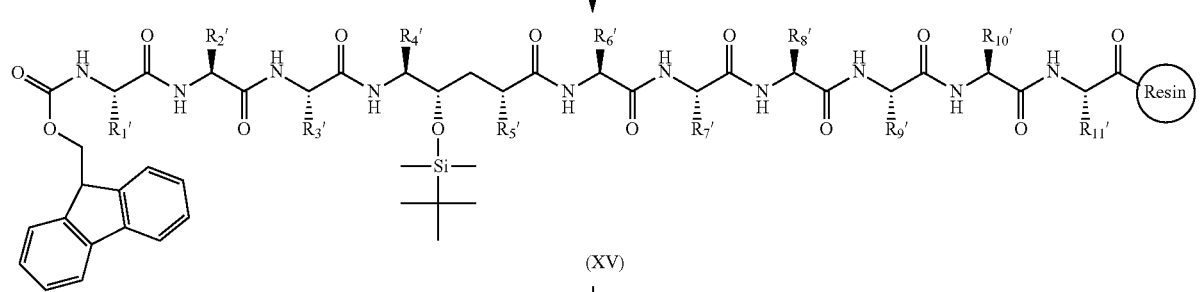
(XV)
Fmoc deprotection or Fmoc deprotection and capping
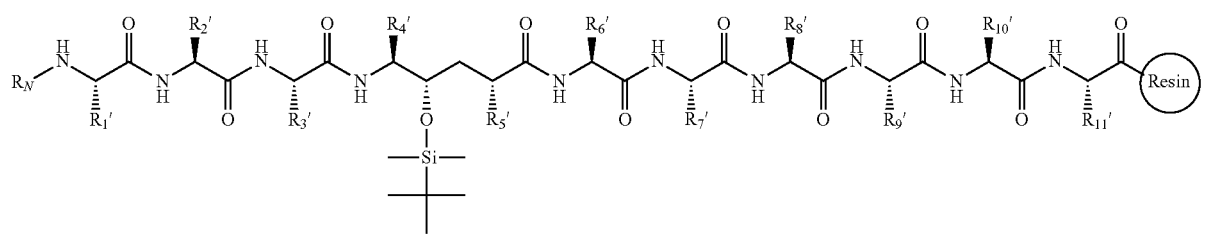
(XVI)
Resin cleavage and deprotection

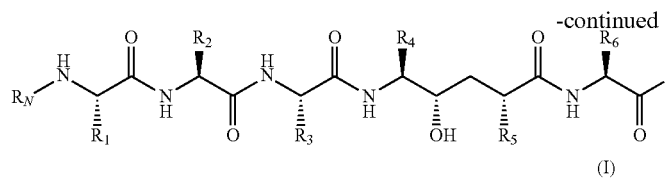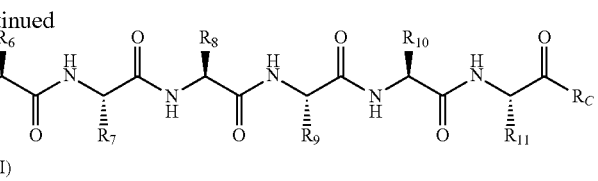

in which:
- $R_1$ represents —H, —CH$_2$CH$_2$SCH$_3$, —CH$_2$CONH$_2$, —CH$_2$CH$_2$CONH$_2$, —CH$_2$COO$^-$ or —CH$_2$CH$_2$COO$^-$;
- $R_2$ represents —CH(CH$_3$)$_2$, —CH$_2$CH(CH$_3$)$_2$, (1S)—CH (CH$_3$)CH$_2$CH$_3$, —CH$_2$-(4-(1H-imidazol-3-ium)) or —CH$_2$CH$_2$COO$^-$;
- $R_3$ represents —CH$_3$, —CH$_2$CH(CH$_3$)$_2$, —CH$_2$-phenyl, —CH$_2$-phenol, —CH$_2$CH$_2$SCH$_3$, —CH$_2$OH, —CH$_2$CONH$_2$, —CH$_2$COO$^-$ or —CH$_2$CH$_2$COO$^-$;
- $R_4$ represents —CH$_2$CH(CH$_3$)$_2$, —CH$_2$-phenyl, —CH$_2$-phenol or —CH$_2$CH$_2$SCH$_3$;
- $R_5$ represents —CH$_3$;
- $R_6$ represents —CH$_3$, —CH(CH$_3$)$_2$, —CH$_2$CH(CH$_3$)$_2$ or (1S)—CH(CH$_3$)CH$_2$CH$_3$;
- $R_7$ and $R_8$ are independently selected from —CH$_2$-phenyl, —CH$_2$-phenol or —CH$_2$-(3-indole);
- $R_9$ represents —H, —CH$_3$, —CH(CH$_3$)$_2$, —CH$_2$CH (CH$_3$)$_2$, (1S)—CH(CH$_3$)CH$_2$CH$_3$ or —CH$_2$CH$_2$*CH$_2$, wherein the *CH$_2$ is bonded to the adjacent NH to form a five membered heterocycle;
- $R_{10}$ and $R_{11}$ are independently selected from —CH$_2$COO$^-$ or —CH$_2$CH$_2$COO$^-$;
- $R_N$ represents —H or —COCH$_3$;
- $R_C$ represents —NH$_2$ or —OH, Referring to Scheme 2, the compounds here disclosed are prepared according the following steps:
- a standard Solid Phase Peptide Synthesis for the preparation of compounds with an amide in the C-terminal using Rink amide resin (X) consisting on ten cycles of Fmoc deprotection and amino acids coupling, each cycle includes two Fmoc deprotections, washes, a single coupling with HBTU activated amino acid and additional washes;
- or a standard Solid Phase Peptide Synthesis for the preparation of compounds with a carboxylic acid in the C-terminal using either Fmoc-Asp (Wang resin) or Fmoc-Glu (Wang resin) (XII) consisting on nine cycles of Fmoc deprotection and amino acids coupling, each cycle includes two Fmoc deprotections, washes, a single coupling with HBTU activated amino acid and additional washes;
- optionally, a capping step accomplished with acetic anhydride, after Fmoc deprotection of compound XV, whether the N-terminal of the compound is acylated or free, rendering compound XVI;
- and the deprotection of compound XVI amino acids lateral chains and resin cleavage is the final step that renders compound I herein described.

In the Solid Phase Peptide Synthesis for the preparation of compounds with an amide in the C-terminal, the Fmoc-protected amino acids are sequential added to Rink Amide Resin (X) according to the following cycles:
- In the first cycle is incorporated: Fmoc-Asp(OtBu)-OH or Fmoc-Glu(OtBu)-OH, rendering compound XI;
- In the second cycle is incorporated: Fmoc-Asp(OtBu)-OH or Fmoc-Glu(OtBu)-OH;
- In the third cycle is incorporated: Fmoc-Gly-OH, Fmoc-Ala-OH, Fmoc-Val-OH, Fmoc-Leu-OH, Fmoc-Ile-OH or Fmoc-Pro-OH;
- In the fourth cycle is incorporated: Fmoc-Phe-OH, Fmoc-Tyr(tBu)-OH or Fmoc-Trp(Boc)-OH;
- In the fifth cycle is incorporated: Fmoc-Phe-OH, Fmoc-Tyr(tBu)-OH or Fmoc-Trp(Boc)-OH;
- In the sixth cycle is incorporated: Fmoc-Ala-OH, Fmoc-Val-OH, Fmoc-Leu-OH or Fmoc-Ile-OH, rendering compound XIII;
- In the seventh cycle is incorporated a synthetic Fmoc-dipeptide hydroxyethylene isostere (IX), rendering compound XIV;
- In the eighth cycle is incorporated: Fmoc-Ala-OH, Fmoc-Leu-OH, Fmoc-Phe-OH, Fmoc-Tyr(tBu)-OH, Fmoc-Met-OH, Fmoc-Ser(tBu)-OH, Fmoc-Asn(Trt)-OH, Fmoc-Asp(OtBu)-OH or Fmoc-Glu(OtBu)-OH;
- In the ninth cycle is incorporated: Fmoc-Val-OH, Fmoc-Leu-OH, Fmoc-Ile-OH, Fmoc-His(Trt)-OH or Fmoc-Glu(OtBu)-OH;
- And in the tenth cycle is incorporated: Fmoc-Gly-OH, Fmoc-Met-OH, Fmoc-Asn(Trt)-OH, Fmoc-Gln(Trt)-OH, Fmoc-Asp(OtBu)-OH or Fmoc-Glu(OtBu)-OH, rendering compound XV.

In the Solid Phase Peptide Synthesis for the preparation of compounds with a carboxylic acid in the C-terminal, the Fmoc-protected amino acids are sequential added according to the following cycles:
- In the first cycle is incorporated: Fmoc-Asp(OtBu)-OH or Fmoc-Glu(OtBu)-OH;
- In the second cycle is incorporated: Fmoc-Gly-OH, Fmoc-Ala-OH, Fmoc-Val-OH, Fmoc-Leu-OH, Fmoc-Ile-OH or Fmoc-Pro-OH;
- In the third cycle is incorporated: Fmoc-Phe-OH, Fmoc-Tyr(tBu)-OH or Fmoc-Trp(Boc)-OH;
- In the fourth cycle is incorporated: Fmoc-Phe-OH, Fmoc-Tyr(tBu)-OH or Fmoc-Trp(Boc)-OH;
- In the fifth cycle is incorporated: Fmoc-Ala-OH, Fmoc-Val-OH, Fmoc-Leu-OH or Fmoc-Ile-OH, rendering compound XIII;
- In the sixth cycle is incorporated a synthetic Fmoc-dipeptide hydroxyethylene isostere (IX), rendering compound XIV;
- In the seventh cycle is incorporated: Fmoc-Ala-OH, Fmoc-Leu-OH, Fmoc-Phe-OH, Fmoc-Tyr(tBu)-OH, Fmoc-Met-OH, Fmoc-Ser(tBu)-OH, Fmoc-Asn(Trt)-OH, Fmoc-Asp(OtBu)-OH or Fmoc-Glu(OtBu)-OH;

In the eighth cycle is incorporated: Fmoc-Val-OH, Fmoc-Leu-OH, Fmoc-Phe-OH, Fmoc-Ile-OH, Fmoc-His(Trt)-OH or Fmoc-Glu(OtBu)-OH;

In the ninth cycle is incorporated: Fmoc-Gly-OH, Fmoc-Met-OH, Fmoc-Asn(Trt)-OH, Fmoc-Gln(Trt)-OH, Fmoc-Asp(OtBu)-OH or Fmoc-Glu(OtBu)-OH, rendering compound XV.

This procedure of scheme 2 is also fully described in Example 2.

The compound of formula I is a peptide based molecule designed to bind BACE-1. The peptide may be prepared as a pharmaceutically acceptable salt, or it may exist in its native charged state. It is based on the sequence of native amyloid precursor protein (APP), however, since it contains the hydroxyethylene bond isostere, is not capable of being hydrolyzed by the enzyme, thereby inhibiting cleavage of APP to A.

EXAMPLES

Example 1—Synthesis of a Compound of Formula IX

To a stirred solution of compound II, N-(tert-Butyloxycarbonyl)-L-leucine, (5.00 g, 21.6 mmol) in dry dichloromethane (DCM) (100 mL) under Ar atmosphere at room temperature, N,O-dimethylhydroxyamine hydrochloride (DMHA) (3.16 g, 32.4 mmol) was added. The resulting mixture was stirred for 10 minutes at room temperature. 4-Methylmorpholine (2.4 mL, 21.6 mmol) was added dropwise. In a separate flask, EDC (6.21 g, 32.4 mmol) was dissolved in dichloromethane (20 mL) under Ar atmosphere. The resulting mixture was added dropwise to the above solution of N,O-dimethylhydroxyamine hydrochloride and 4-Methylmorpholine.

The reaction mixture was kept stirring, under Ar atmosphere at room temperature for 2 days. The reaction was quenched with water and the layers were separated. The aqueous layer was extracted with dichloromethane (3×50 mL). The organic layer was dried over anhydrous $MgSO_4$ and concentrated under reduced pressure. Compound III was obtained as a pale yellow oil (5.63 g, 95%). Compound III: $^1$H NMR (400 MHz, $CDCl_3$) δ 5.06 (broad d, 1H, J=8.9 Hz), 4.72 (m, 1H), 3.79 (s, 3H), 3.20 (s, 3H), 1.72 (m, 1H), 1.46-1.36 (m, 2H), 1.43 (s, 9H), 0.97 (d, 3H, J=6.5 Hz), 0.93 (d, 3H, J=6.6 Hz; $^{13}$C NMR (100 MHz, $CDCl_3$) δ 156.7, 155.7, 79.5, 61.6, 56.1, 49.0, 41.8, 28.4, 24.7, 23.3, 21.6.

To a stirred suspension of lithium aluminium hydride ($LiAlH_4$) (711 mg, 18.8 mmol) in dry diethyl ether (85 mL) at −98° C. under Ar atmosphere, was added compound III, N-(tert-Butyloxycarbonyl)-L-leucine-N'-methoxy-N'-methylamide, (5.14 g, 18.7 mmol) in dry diethyl ether (20 mL). The reaction mixture was kept stirring, under Ar atmosphere while temperature was raised from −98° C. to −70° C. for 45 minutes. The reaction was quenched with ethyl acetate and with a saturated solution of ammonium chloride. The resulting mixture was warmed to 25° C. while stirring. The resulting solution was filtered and the solid residue was washed twice with diethyl ether. The filtrate was extracted with dichloromethane (3×50 mL). The organic layer was washed with saturated sodium bicarbonate, dried over anhydrous $MgSO_4$ and concentrated under reduced pressure. The residue was immediately used without purification and it was dissolved in tetrahydrofuran (100 mL) and kept at −98° C. To a stirred solution of diisopropylamine (7.89 mL, 56.3 mmol) in dry tetrahydrofuran (THF) (50 mL) at 0° C. under Ar atmosphere, was added n-butyllithium (1.6M in hexane, 32.8 mL, 52.5 mmol) dropwise. The resulting solution was stirred at 0° C. for 15 minutes, and then cooled to −78° C. To this solution was added a benzyl propargyl ether (8.2 g, 56.3 mmol) solution in tetrahydrofuran (50 mL) dropwise. The resulting solution was kept stirring, under Ar atmosphere at −78° C. for 30 minutes and then was added the above solution containing the residue of the non-purified aldeyde through a cannula, dropwise, over a period of 15 minutes. The reaction mixture was kept stirred, under Ar atmosphere at −78° C. for 45 minutes. The reaction was quenched adding the reaction mixture through a cannula into a stirred saturated solution of ammonium chloride. The aqueous layer was extracted with dichloromethane (3×50 mL). The combined organic layers were dried over anhydrous $MgSO_4$ and concentrated under reduced pressure. The residue was purified by flash silica gel chromatography (30% ethyl acetate/hexane) to yield compound IV (2.83 g, 42%) as colourless oil.

Compound IV: $^1$H NMR (400 MHz, $CDCl_3$) δ 7.38-7.27 (m, 5H), 4.61 (broad s, 1H), 4.59 (s, 2H), 4.41 (d, 1H, J=4.5 Hz), 4.21 (s, 2H), 3.79 (m, 1H), 2.39 (broad s, 1H), 1.70 (m, 1H), 1.55-1.35 (m, 2H), 1.44 (s, 9H), 0.95 (d, 3H, J=6.6 Hz), 0.93 (d, 3H, J=6.6 Hz); $^{13}$C NMR (100 MHz, $CDCl_3$) δ 156.3, 137.3, 128.5, 128.1, 127.9, 85.4, 81.7, 79.7, 71.6, 65.5, 57.4, 53.3, 39.3, 28.4, 24.8, 23.5, 21.8; HRMS: m/z $[M+H]^+$ calculated for $C_{21}H_{31}NNaO_4$=384.2145, found=384.2135; FT-IR (ATR): 1689.34, 1953.61, 3400.61 $cm^{-1}$.

To 10% Pd/C (0.37 g) was added methanol (30 mL) and then a solution of the diasteriomeric mixture of compound IV, (4S,5S)- and (4R,5S)-5-[(tert-Butyloxycarbonyl)amino]-1-benzyloxy-7-methyl-2-octyn-4-ol, (5.39 g, 14.9 mmols) in methanol (10 mL) was added. The resulting mixture was hydrogenated at 30 psi for 2 hours and after this period pressure was raised to 50 psi for 20 hours. The reaction mixture was filtered through a plug of Celite and the filtrate was concentrated under reduced pressure. The residue was purified by flash silica gel chromatography (70% ethyl acetate/hexane) to yield compound V (10 g, 76%) as colourless oil. Compound V: $^1$H NMR (400 MHz, $CDCl_3$) δ 4.84 (s, 1H), 3.75-3.40 (m, 6H), 1.76-1.39 (m, 7H), 1.44 (s, 9H), 0.92 (d, 6H, J=3.2 Hz); $^{13}$C NMR (100 MHz, $CDCl_3$) δ 156.5, 79.2, 73.8, 62.6, 52.7, 41.6, 31.5, 29.3, 28.4, 24.8, 23.2, 22.1; HRMS: m/z $[M=H]^+$ calculated for $C_{14}H_{29}NNaO_4$=298.1989, Found=298.1988; FT-IR (ATR): 1682.28, 3349.67 $cm^{-1}$.

To a stirred solution of the diasteriomeric mixture of compound V, (4S,5S)- and (4R,5S)-5-[(tert-Butyloxycarbonyl)amino]-7-methyloctane-1,4-diol, (1.10 g, 4.0 mmol) in dry dichloromethane (80 mL) at 25° C. was added BAIB (3.87 g, 12.0 mmol) followed by the addition of TEMPO (0.125 g, 0.8 mmol). The resulting mixture as stirred at 25° C. for 15 hours. The reaction mixture was quenched with a saturated solution of sodium thiosulfate. The aqueous layer was extracted with dichloromethane (3×50 mL). The combined organic layers were washed with saturated sodium bicarbonate, dried over anhydrous $MgSO_4$ and concentrated under reduced pressure. The residue was purified by flash silica gel chromatography (30% ethyl acetate/hexane) to yield compound VI (0.98 g, 68%) as a yellow solid. Compound VI: $^1$H NMR (400 MHz, $CDCl_3$) δ 4.61-4.46 (m, 2H), 3.86 (m, 1H), 2.52 (t, 2H, J=8.4 Hz), 2.29-2.06 (m, 2H), 1.74-1.24 (m, 3H), 1.44 (s, 9H), 0.94 (d, 3H, J=6.6), 0.93 (d, 32, J=6.5); $^{13}$C NMR (100 MHz, $CDCl_3$) δ 177.4, 156.1, 82.5, 79.7, 51.0, 42.1, 28.6, 28.3, 24.7, 24.2, 23.0, 21 0.9; $[α]_D^{20}$=−29.4° (c 1.0, $CH_3OH$).

To a stirred solution of diisopropylamine (2.46 mL, 17.6 mmol) in dry tetrahydrofuran (20 mL) at 0° C. under Ar atmosphere, was added n-butyllithium (1.6M in hexane, 10.5 mL, 16.8 mmol) dropwise. The resulting solution was stirred at 0° C. for 15 minutes, and then cooled to −78° C. The resulting solution was added dropwise through a cannula to a stirred solution of the compound VI, (5S,1'S)-5-[1'-[(tert-Butyloxycarbonyl)amino]-3'-methylbutyl]-dihydrofuran-2(3H)-one, (2.02 g, 7.48 mmol) in dry tetrahydrofuran at −78° C. under Ar atmosphere. The resulting solution was kept stirring, under Ar atmosphere at −78° C. for 60 minutes and then was added iodomethane (1.1 mL, 17.6 mmol) dropwise. The reaction mixture was kept stirring, under Ar atmosphere at −78° C. for 20 minutes. The reaction was quenched with a saturated solution of ammonium chloride. The aqueous layer was extracted with dichloromethane (3×50 mL). The combined organic layers were dried over anhydrous $MgSO_4$ and concentrated under reduced pressure. The residue was purified by flash silica gel chromatography (15% ethyl acetate/hexane) to yield compound VII (1.62 g, 76%) as an amorphous solid.

Compound VII: $^1$H NMR (400 MHz, $CDCl_3$) δ 4.50 (broad t, 1H, J=6.1 Hz), 4.38 (d, 1H, J=9.6 Hz), 3.84 (m, 1H), 2.69 (m, 1H), 2.40 (m, 1H), 1.94 (m, 1H), 1.67-1.34 (m, 3H), 1.43 (s, 9H), 1.28 (d, 3H, J=7.4 Hz), 0.94 (d, 3H, J=6.6), 0.92 (d, 3H, J=6.5); $^{13}$C NMR (100 MHz, $CDCl_3$) δ 180.5, 156.1, 80.3, 79.8, 51.5, 42.0, 34.4, 32.5, 28.3, 24.8, 23.1, 21.8, 16.7.

To a stirred solution of compound VII, (3R,5S,1'S)-5-[1'-[(tert-Butyloxycarbonyl)amino]-3'-methylbutyl]-3-methyl-dihydrofuran-2(3H)-one, (1.62 g, 5.7 mmol) in tetrahydrofuran (10 mL) was added a aqueous solution of lithium hydroxide (29 mL, 29 mmol). The resulting solution was stirred at 25° C. for 16 hours and after that period was concentrated under reduced pressure. The residue was cooled to 0° C. and a 25% citric acid solution was added till pH=4. The resulting solution was extracted with ethyl acetate (3×50 mL). The combined organic layers were washed with brine and dried over anhydrous $MgSO_4$. Evaporation of the solvent afforded the hydroxy acid (1.76 g) that was used for the next reaction without further purification. To this hydroxyl acid (1.76 g, 5.7 mmol) in dry dimethylformamide (DMF) (80 mL) was added imidazole (8.3 g, 122 mmol) and TBDMSCl (9.2 g, 61 mmol). The reaction mixture was stirred at 23° C. for 22 hours. To the reactional mixture was added methanol (20 mL) and the mixture was stirred for 1 hour. The reaction was quenched with a 25% citric acid solution. The mixture was extracted with ethyl acetate (3×100 mL). The combined organic layers were washed with brine, dried over anhydrous $MgSO_4$ and concentrated under reduced pressure. The residue was purified by flash silica gel chromatography (30% ethyl acetate/hexane) to yield compound VIII (1.66 g, 69%) as an oil. Compound VIII: $^1$H NMR (400 MHz, $CDCl_3$) δ 4.53 (d, 1H, J=9.6 Hz), 3.68-3.57 (m, 2H), 2.53 (m, 1H), 1.79 (m, 1H), 1.55 (m, 1H), 1.40-1.25 (m, 1H), 1.18 (m, 2H) 1.37 (s, 9H), 1.12 (d, 3H, J=6.8 Hz), 0.86 (d, 6H), 0.82 (s, 9H), 0.00 (s, 3H), −0.08 (s, 3H). $^{13}$C NMR (100 MHz, $CDCl_3$) δ 178.8, 156.9, 80.0, 72.1, 50.6, 41.4, 38.0, 36.1, 28.4, 25.9, 24.9, 23.1, 22.2, 16.8, −4.3, −4.5.

To a stirred solution of the compound VIII, (2R,4S,5S)-5-[(tert-Butyloxycarbonyl)amino]-4-[(tert-Butyldimethylsilyl)oxy]-2,7-dimethyloctanoic acid, (1.13 g, 2.7 mmol) in dichloromethane (25 mL) at 0° C. was added trifluoroacetic acid (6.5 mL) in four portions during 1 hour, while the reaction was monitored by TLC. After the reaction occurred the solvent was removed under reduce pressure and not exceeding 5° C. To the residue was added dioxane (12.5 mL) and the solution was stirred. To the resulting solution was added 1M of aqueous $NaHCO_3$ (42 mL). To the resulting solution was added Fmoc-succinimide (FMOC-OSu) (1.09 g, 3.2 mmol) in dioxane. The reaction mixture was stirred at 25° C. overnight. The reaction mixture was then diluted with distilled water (40 mL) and acidified with a 25% citric acid solution till pH=4. The solution was then extracted with ethyl acetate (3×50 mL). The combined organic layers were washed with brine, dried over anhydrous $MgSO_4$ and concentrated under reduced pressure. The residue was purified by flash silica gel chromatography (30% ethyl acetate/hexane) to yield compound IX, (2R,4S,5S)-5-[(Fluorenyl-methyloxycarbonyl) amino]-4-[tert-butyldimethylsilyl)oxy]-2,7-dimethyloctanoic acid (0.76 g, 52%) as a white foam.

Compound IX: $^1$H NMR (400 MHz, DMSO-$d^6$) δ 7.89 (d, 2H, J=7.5 Hz), 7.70 (dd, 2H, J=7.4, 12.3), 7.41 (t, 2H, J=7.4 Hz), 7.32 (m, 2H), 7.20 (d, 1H, J=8.4 Hz), 4.28-4.21 (m, 3H), 3.68-3.54 (m, 2H), 2.44 (m, 1H), 1.84 (m, 1H), 1.56 (m, 1H), 1.34-1.08 (m, 3H), 1.10 (d, 3H, J=3.6 Hz) 0.87 (s, 9H), 0.83 (d, 3H, J=5.7), 0.80 (d, 3H, J=6.7) 0.09 (s, 3H), 0.05 (s, 3H).

Example 2—Synthesis of a Compound of Formula I

This compound was synthesized following a manual standard Solid Phase Peptide Synthesis procedure. This procedure is characterized by successive deprotection/coupling cycles to assemble the amino acids into a peptide. These cycles include both a deprotection and a coupling step. In the deprotection step Fmoc is removed from the amino terminus. For this, 20% piperidine in dimethylformamide (15 mL) is added to the resin and the reaction mixture is stirred at 25° C. under nitrogen atmosphere for 15 minutes. After this time the reaction mixture is filtered using vaccum and resin is washed with dimethylformamide (6 mL). This deprotection step is repeated twice to assure complete Fmoc deprotection. Completion of this step it is monitored by TLC (diethyl ether:hexane (3:2)) by UV-Vis spectroscopy following the release of the Fmoc protecting group. In the coupling step Fmoc protected amino acids are added to the resin. For this, to the stirred resin at 25° C. under nitrogen atmosphere in dimethylformamide (6 mL) is added a coupling mixture consisting of 2 equivalents of Fmoc protected amino acid, 1-hydroxybenzotriazole (HOBt) and HBTU in dimethylformamide (4 mL). HOBt is used in the same equivalent amount of amino acid while for HBTU only 0.95 equivalents are used. To the resulting mixture is added 4 equivalents of N,N-diisopropylethylamine (DIEA) in N-Methyl-2-pyrrolidone (NMP) (2 mL). The reaction mixture is stirred at 25° C., under nitrogen atmosphere for 1 hour. Afterwards, the reaction mixture is filtered and washed twice with dimethylformamide. This describes one deprotection/coupling cycle of peptide synthesis.

One thousand six hundred ninety five milligrams of Rink Amide MBHA resin (100-200 mesh), 1.00 mmol, were placed in a glass reactor suitable for manual synthesis. The resin was swollen twice with dichloromethane (2×15 mL) for 30 minutes followed by dimethylformamide (2×15 mL) for 15 minutes, under nitrogen atmosphere. Solvent was removed between additions by vacuum filtration. Two millimole of Fmoc-Asp(OtBu)-OH, Fmoc-Glu(OtBu)-OH, Fmoc-Ala-OH, Fmoc-Tyr(tBu)-OH, Fmoc-Phe-OH and Fmoc-Val-OH were consecutively and sequentially coupled to the Fmoc deprotected resin, by means of successive deprotection/coupling cycles, as described above. After the assembling of the first six amino acids, seven hundred and five milligrams of the compound of formula IX (1.3 mmol) were coupled using the above described deprotection/coupling cycle, except that in this coupling step the compound of formula IX was dissolved in NMP instead of dimethylformamide. After coupling of compound of formula IX, two millimol of Fmoc-Asp(OtBu)-OH, Fmoc-Leu-OH and Fmoc-Glu(OtBu)-OH were consecutively and sequentially coupled to the Fmoc deprotected resin, by means of successive deprotection/coupling cycles. After the coupling of glutamic acid, the Fmoc group was removed from the resin as already described above and the free amine group was capped. To the stirred resin in dimethylformamide (10 mL) was added a solution of 1.6 mL of acetic anhydride and 1.6 mL of DIEA in 0.8 mL of dimethylformamide. The reaction mixture was stirred at 25° C., under nitrogen atmosphere for 1 hour. After this time the reaction mixture was filtered, washed twice with dimethylformamide followed by dichloromethane and dried under nitrogen flux. To the dried resin 10 mL of a solution of trifluoroacetic acid, triisopropylsilane and water (95:2.5:2.5) were added. The reaction mixture was stirred at 25° C., under nitrogen atmosphere for 2 hours. The reaction mixture was filtered and the filtrate was concentrated under nitrogen flow. The addition of cold ethyl ether rendered a white precipitate that was collected by vacuum filtration. The precipitate was washed with cold ethyl ether and dried in vacuum. The residue was purified using preparative reverse phase HPLC (Column: Phenomenex Jupiter 4 μm Porteo 90 Å, C12, 250×21.2 mm, Flow: 10 mL/min, Gradient=20% B to 55% B over 30 minutes (A=99.9% water/0.1% TFA; B=90% $CH_3CN$/9.9% water/0.1% TFA)), to yield the compound of formula I (570 mg, 43%). Re-analysis by reverse phase analytical HPLC and ESI-MS is in accordance with a homogenous product (m/z calculated=1326.48, m/z observed=1326.34).

Example 3—Influence of Conjugation of the Compound OM00-3 with A/β 17-23' on BACE-1 Inhibition Potency An assay for BACE-1 activity was accomplished in order to test the effective BACE-1 inhibition when OM00-3 is conjugated with Aβ 17-23'. Therefore, kinetic experiments were performed in 20 mM sodium acetate buffer, pH 4.5 at 37° C. in 15% dimethyl sulfoxide (DMSO), 1% triton X-100 (Sigma-Aldrich), 250 nM of Mca-SEVNLDAEFK-DNP (Bachem) as substrate and 2 U/mL of BACE-1 (human, recombinant, 21267 U/mg, purity>90%, Sigma-Aldrich). The initial rates of substrate hydrolysis were confirmed to be directly proportional to the enzyme concentrations in a range of 1-5 U/mL. Initial rates were determined below conversion of 5% of substrate, after stopping the reaction with 25% of a 2.5 M sodium acetate solution after 2 hours. The hydrolysis of the fluorogenic substrate was quantified by reverse phase HPLC with fluorescence detection (HPLC-FLU) using an excitation wavelength of 323 nm and an emission wavelength of 382 nm (Merck Hitachi, Elite LaChrom). A C18 column (Gemini, Phenomenex) 150 mm, 4.60 mm, 5 μm was used at 30° C. with a linear gradient from (A) water/TFA (99.9:0.1, V/V), to (B) acetonitrile/water/TFA (90:9.9:0.1, V/V) at 1 mL/min. The program started at 90% A for two min, graded to 70% A during ten min and finally to 0% A during two min. The retention time of the reaction product (Mca-SEVNL-COOH) was 11 minutes and quantification was performed by external calibration.

Figure 2:
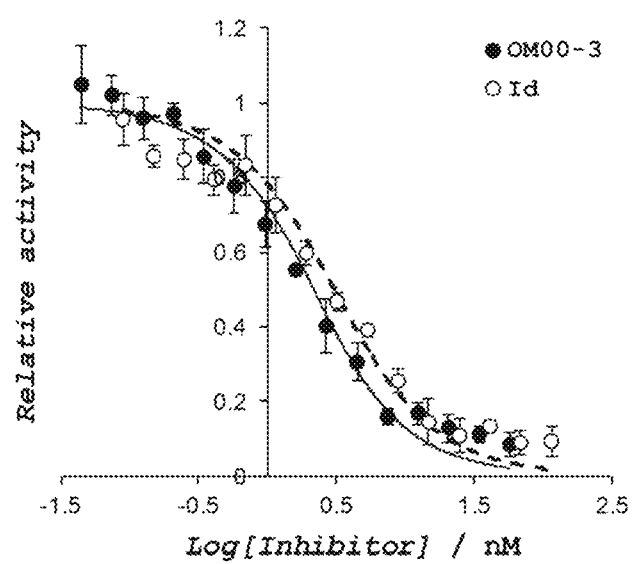
FIG. 2 illustrates the comparison of BACE-1 inhibition profiles by one of the most potent known peptidomimetic β-secretase inhibitors, the OM00-3 (1.2±0.4 nM) and compound of formula Id (2.0±0.1 nM) (mean value±standard deviation, n=3).

As illustrated in FIG. 2, conjugation affects the potency of the inhibitor to only a very small extent ($K_{i\ (compound\ Ic)}$=2.0±0.1 nM vs. $K_{i\ (OM00-3)}$=1.2±0.4 nM, mean value±standard deviation, n=3, p≤0.05, independent two-tailed Student's t-test). The value reported here for the Ki of OM00-3 is four-fold higher than the previously reported value of 0.31 nM. This is due to the fact that a permanently active form of BACE-1 was used before, while in the present study a pro-BACE-1 was employed possessing a pro domain in equilibrium with an opened and closed form, leading to a reduction of the enzyme activity. For a similar inhibitor, OM99-2, a seven-fold potency decrease was observed when pro-BACE-1 ($K_i$=9.8 nM) was used instead of active BACE-1 ($K_i$=1.4 nM). Moreover, the potency decrease observed for Id (about two-fold) in comparison with OM00-3, is less than that reported for the conjugation of OM99-2 with a carrier peptide of the Tat protein of HIV-1 or when OM00-3 was conjugated with a nonapeptide of arginines, where the inhibition potency over the active form of BACE-1 decreased twenty eight (39 nM) and six-fold (1.7 nM), respectively, when compared to the reported value of 0.31 nM.

Example 4—Effect of the Exchange of a Phenylalanine by a Tyrosine at Position with Lateral Chain $R_8$ An assay for BACE-2 activity was accomplished in order to test the effective BACE-2 inhibition. Therefore, kinetic experiments were performed in 20 mM sodium acetate buffer, pH 4.5 at 37° C. in 15% dimethyl sulfoxide (DMSO), 1% triton X-100 (Sigma-Aldrich), 250 nM of Mca-SEVN- LDAEFK-DNP (Bachem) as substrate and 10 U/mL of BACE-2 (human, recombinant, 40000 U/mg, purity>80%, Enzo). The initial rates of substrate hydrolysis were confirmed to be directly proportional to the enzyme concentrations in a range of 5-20 U/mL for BACE-2. Initial rates were determined below conversion of 5% of substrate, after stopping the reaction with 25% of a 2.5 M sodium acetate solution after 1 hour. The hydrolysis of the fluorogenic substrate was quantified by reverse phase HPLC with fluorescence detection (HPLC-FLU) using an excitation wavelength of 323 nm and an emission wavelength of 382 nm (Merck Hitachi, Elite LaChrom). A C18 column (Gemini, Phenomenex) 150 mm, 4.60 mm, 5 μm was used at 30° C. with a linear gradient from (A) water/TFA (99.9:0.1, V/V), to (B) acetonitrile/water/TFA (90:9.9:0.1, V/V) at 1 mL/min. The program started at 90% A for two min, graded to 70% A during ten min and finally to 0% A during two min. The retention time of the reaction product (Mca-SEVNL-COOH) was 11 minutes and quantification was performed by external calibration.

The results reported for the preference of amino acids at the eight subsites of BACE-1 and BACE-2 substrates reveal that the preference index for phenylalanine at position with lateral chain $R_8$ (FIG. 1) in the case of BACE-2 is very high when compared to the null preference index for tyrosine, while it is similar to the one for tyrosine in the case of BACE-1. This means that an exchange of a phenylalanine by a tyrosine in Id should have little effect on the inhibition of BACE-1 while significantly reduce affinity for BACE-2. Also, this change should have minimal effect on RAGE binding since tyrosine, like phenylalanine, is a hydrophobic aromatic amino acid, which is a requisite for RAGE binding.

Figure 3:
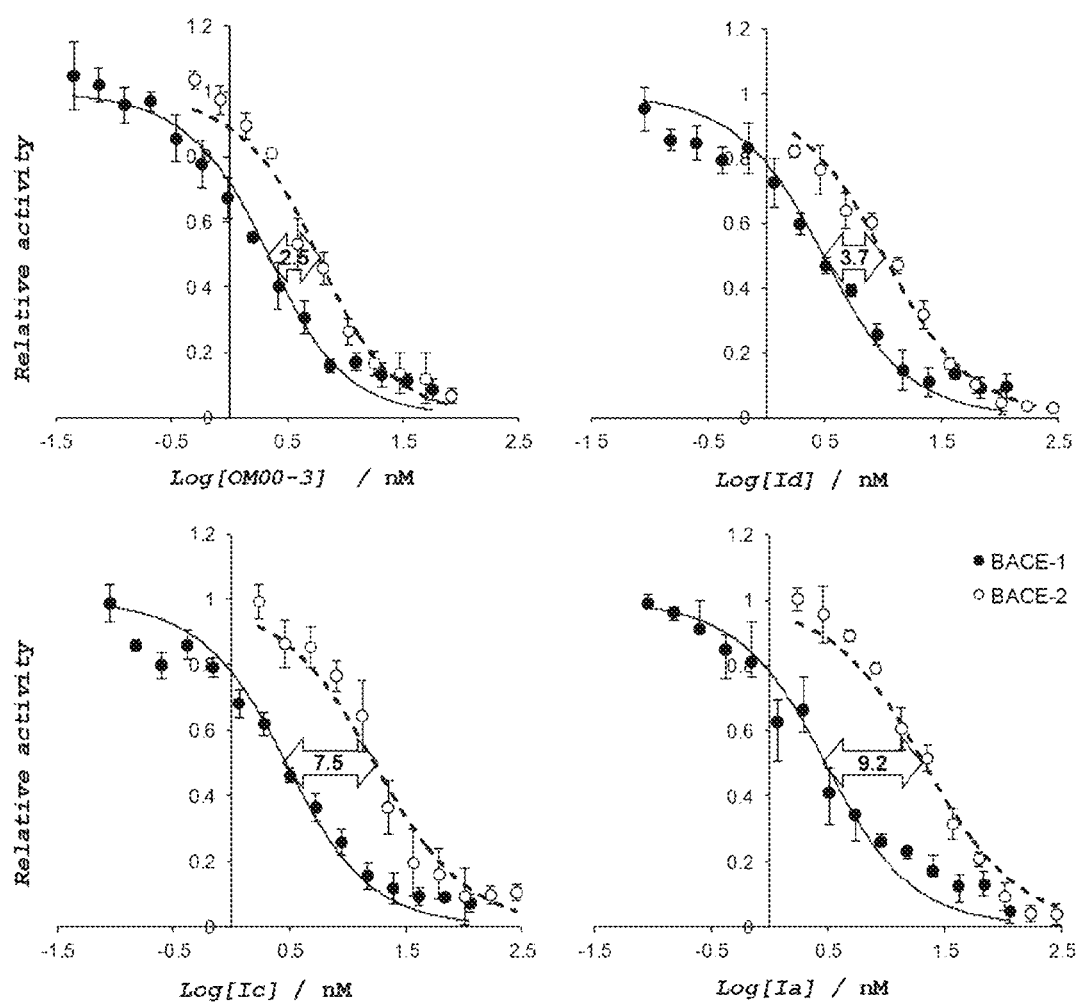
FIG. 3 illustrates the comparison between the inhibition profiles of BACE-1 and BACE-2, by OM00-3 and compounds of formula Id, Ic and Ia (mean value±standard deviation, n=3). The $K_i^{app}{}_{BACE-2}/K_{i\ BACE-1}$ ratio is 2.5 for OM00-3, 3.7 for Id, 7.5 for Ic and 9.2 for Ia.

As outlined in FIG. 3, compound Ic shows a ratio between $K_i^{app}{}_{BACE-2}$ and $K_{i\ BACE-1}$ of 7.5, which is higher than that of Id (3.7) and of 1 (2.5). The design of Ic lead therefore to an inhibitor two-fold more selective than Id, which in its turn was already more selective than OM00-3, indicating that conjugation with the carrier peptide also contributes to increase the selectivity for BACE-1 in relation to BACE-2.

Example 5—Influence of N-Terminal Acylation on the Metabolization Profile

An assay for in vitro metabolic stability was accomplished in order to test the influence of N-terminal acylation on the metabolization profile of the compounds. Therefore, compounds were prepared at 50 μM in phosphate-buffered saline (PBS) with 2% DMSO. An amount of 10 μL of the solution was added to human serum (40 μL) or to 10% of mice brain homogenate in PBS with 0.5% Triton X-100 (40 μL). All compounds were tested using the same biological samples of human serum and mice brain homogenate to ensure identical deactivation conditions. The solutions were incubated during different time periods at 37° C., after which metabolization was stopped by adding one volume of acetonitrile. Precipitated serum and brain proteins were removed by centrifugation at 14 000g for 10 min. Tests were made confirming that acetonitrile does not precipitate the synthetic peptides. The remaining peptide in the supernatant was quantified by HPLC-FLU (Merck Hitachi, Elite LaChrom), (ex$\lambda$=255 nm and em$\lambda$=285 nm, to detect compounds containing phenylalanine, and ex$\lambda$=275 nm and em$\lambda$=307 nm whenever tyrosine is present). Chromatographic conditions were as described for determination of enzyme activities. A calibration curve was built for each compound, and the decay in the concentration of the peptide in the incubated samples was followed until approximately 50% decay. The metabolization kinetics of the synthetic peptides followed a monophasic behaviour in vitro.

Figure 4:
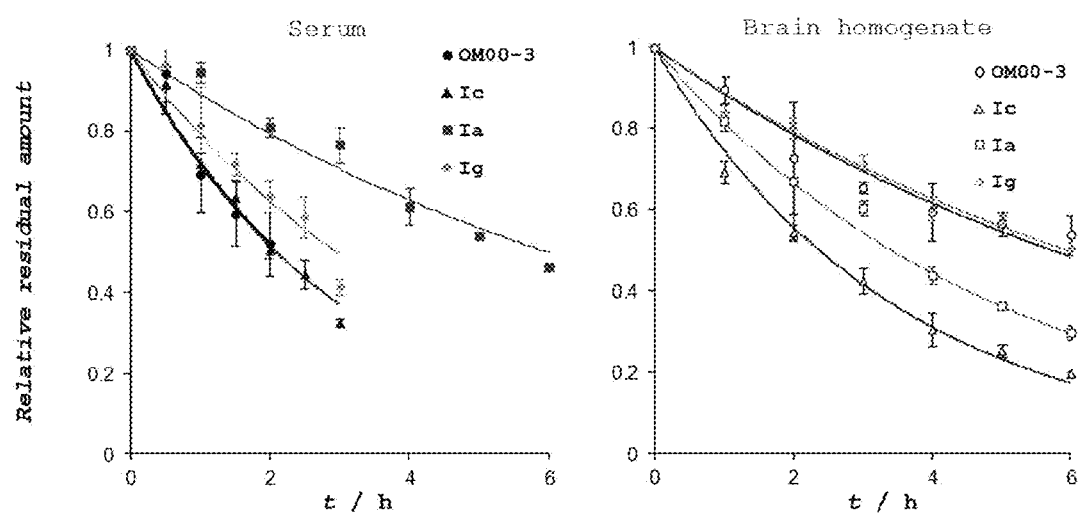
FIG. 4 illustrates the metabolization profile of OM00-3 ($t_{1/2\ serum}$=2.2±0.5; $t_{1/2\ brain}$=5.8±0.7), Ic ($t_{1/2\ serum}$=2.1±0.1; $t_{1/2\ brain}$=2.3±0.1), Ia ($t_{1/2\ serum}$=6.0±0.2; $t_{1/2\ brain}$=3.43±0.1) and Ig ($t_{1/2\ serum}$=3.0±0.2; $t_{1/2\ brain}$=6.0±0.3) (mean value±standard deviation, n=3).

A comparative metabolic stability study of OM00-3, Ic and Ia was carried out through in vitro incubation in Human serum and mice brain homogenate. Half-lives were determined from the exponential metabolization profiles shown in FIG. 4. N-acylation contributed significantly to stability as the half-lives of Ia increased three-fold in serum and two-fold in brain homogenate, compared to those of Ic. The carrier peptide Aβ 17-23' caused however some detrimental effect in the stability of OM00-3 in brain homogenate since OM00-3 is two-fold more stable than Ic. The metabolization half-lives of Ia in serum (6.0 hours) and brain homogenate (3.4 hours) indicate potential for its use as a drug. Some previously reported peptides tested for the treatment of Alzheimer's disease only last a few minutes in mice brain homogenate even after N-terminal protection.

The potency of Ia over BACE-1 is not statistically different from that of OM00-3 having a $K_i$ of 2.0±0.6 (mean value±standard deviation, n=3, p>0.05, independent two-tailed Student's t-test). Finally, among the studied compounds, Ia was also the most selective for BACE-1 in relation to BACE-2 showing a ratio of 9.2 between $K_i^{app}{}_{BACE-2}$ and $K_{i\ BACE-1}$ (FIG. 3), being four-fold more selective than OM00-3.

Example 6—Evaluation of the Cytotoxic Potential in Caco-2 Cells

Human colon carcinoma cells (Caco-2) from the American Type Culture Collection (ATCC HTB-37), between passage number 26 to 41, were routinely cultured in T-75 flasks (BD Biosciences) using high glucose (4.5 g/L) Dulbecco's Modified Eagle Medium (DMEM), supplemented with 10% (v/v) fetal bovine serum (FBS) and 1% (v/v) non-essential aminoacids (Gibco; Grand Island, USA), at 37° C. in a humidified atmosphere containing 5% (v/v) $CO_2$. Once a week, before reaching confluence, cells were cultured using Dulbecco's phosphate buffered saline (DPBS) and 0.25% (w/v) Trypsin-EDTA (Gibco). The cytotoxicity assay was performed using the Promega CellTiter 96 cellular viability assay, MTS, to determine the number of viable cells in culture. Confluent Caco-2 cells were incubated with increasing concentrations of testing compounds from 2.5 nM to 50 μM in 0.5% FBS supplemented DMEM, for 4 hours and 24 hours exposure periods. After the incubation period the medium was removed and 100 μL of MTS mixture was added to each well.

Cells were incubated with MTS for 4 hours at 37° C. with 5% $CO_2$ at fully humidified atmosphere. After the incubation period the absorbance of formazan was read at 490 nm using a plate reader (Biolek™ Power Wave XS). The results were determined as a percentage of the cellular viability in relation to the control composed of cells with 0.5% FBS supplemented DMEM.

Caco-2 cells were used as a preliminary assay to study compounds toxicity. The cytotoxicity assay evaluated the dependence of Caco-2 cell viability with the inhibitor concentration, of compounds: OM00-3, Id, Ic and Ia during incubation periods of 4 and 24 hours. Cellular viability was maintained above 80% within a range of 25 nM to 50 μM for all inhibitors, even after 24 hours demonstrating that the compounds are not toxic up to a concentration magnitude that exceeds their inhibition constant of more than 25 thousand fold.

Example 7—In Vivo Pharmacokinetic Study for Evaluation of Compound Ia Delivery into Brain Female mice (n=12, 8-12 weeks, weighing 22-37 g) and male Wistar rats (n=8, 8-12 weeks, weighing 182-201 g) were purchased from Harlan Ibérica, Barcelona, Spain. All animals received a standard diet and water ad libitum. Experiments were conducted according to the Home Office Guidance in the Operation of Animals (Scientific Procedures) Act 1986, published by Her Majesty's Stationary Office, London, UK and the Institutional Animal Research Committee Guide for the Care and Use of Laboratory Animals published by the US National Institutes of Health (NIH Publication No. 85-23, revised 1996), as well as to the currently adopted EC regulations (2010/63/EU). Finally, the studies are in compliance with the ARRIVE Guidelines for Reporting Animal Research' summarized at www.nc3rs.org.uk. Before experiments animals were fasted for 24 h.

PBS was used to prepare a solution of Ia for intravenous administration at a dose of 0.53 mg/kg. Experiments were done in triplicate. Mice and Wistar rats were sacrificed at 0.5, 1 and 2 hours after dosing and were previously anesthetized with sodium pentobarbital (6 mg/kg i.p.) for collection of blood by cardiac puncture and brain tissue was perfused by intraventricular injection of 10 mL of chilled saline solution to remove residual blood.

Serum was isolated from the blood samples by centrifugation at 657 g for 10 min, at 4° C. Serum proteins were precipitated with one volume of acetonitrile and were removed by centrifugation at 14000 g for 10 min. Brain was promptly removed and washed with PBS and blotted dry. Meninges were carefully removed. In the case of Wistar rats only cortex and hippocampus were collected while for mice the whole brain was used. The brain samples were homogenized with 2 volumes (V/w) of PBS/acetonitrile/Triton X-100 (50/50/0.5) using firstly a pestle and then a pipette and finally a sonicator. Compound Ic was added as internal standard to best mimic the recovery of compound Ia. The pellet was removed centrifuging at 14000 g for 10 min. Samples were purified by preparative reverse-phase HPLC Using a C18 column (Jupiter, Phenomenex) 250×21.2 mm, 5 μm. Chromatographic conditions were as follow: eluent (A) water/TFA (99.9:0.1, V/V), (B) acetonitrile/water/TFA (90:9.9:0.1, V/V). The linear gradient was started at 80% A, graded to 68% for 2 min and then was kept at 68% for 17 min finally grading to 0% A for 5 min. The flow rate was 10 mL/min and the column was at room temperature. Collected fractions (100 ml) were lyophilized, reconstituted in 200 μL of PBS and stored at −20° C. prior analysis.

Mice samples were analyzed for detection of the compounds (Ia and their metabolites) by HPLC-FLU using an excitation wavelength of 275 nm and an emission wavelength of 307 nm, as well as by LC-ESI-MS (LTQ, ThermoFinigan) in the positive mode. Mass range was measured from 250-2000 amu. The ESI source conditions were adjusted as follows: source capillary operating at 5 kV and source temperature at 300° C. A full-scan MS method in positive mode was used for sample analysis of the molecular ions: $[M+H]^+$, $[M+Na]^+$ of Ia as well as its metabolites. The chromatographic step was performed in a C8 column (LiChroCART, Merck) 100 mm×4.6 mm, 5 μm at 30° C. and 1 mL/min, under the following conditions: eluent (A) water/formic acid (99.9:0.1, V/V), (B) acetonitrile/water/formic acid (90:9.9:0.1, V/V). Water and acetonitrile were of LC-MS grade. The linear gradient was initially at 80% A and graded to 65% eluent A during 27 min, and to 0% eluent A for another minute.

For identification of Ia and its metabolite in Wistar rat brain, samples were analyzed using a 4800plus MALDI-TOF/TOF (AB Sciex) mass spectrometer in the positive reflector MS and MS/MS modes with 3200 laser shots per spectrum and data was collected using the 4000 Series Explorer Software v.3.5.3 (Applied Biosystems). The maximum precursor mass tolerance (MS) was 50 ppm and the maximum fragment mass tolerance (MS/MS) was 0.3 Da. 0.6 μL of each sample was directly spotted on a MALDI plate and 0.6 μL α-Cyano-4-hydroxycinnamic acid (CHCA) matrix (LaserBio Labs; 5 mg/ml in 50% (V/V) acetonitrile with 5% (v/v) formic acid) was added.

For confirmation purposes of the metabolite found in vivo, Ig was produced from Ic: 200 μM of Ic were hydrolyzed in a 500 mM aqueous solution of Sodium Hydroxide overnight. Reaction was stopped at pH=7 with acetic acid and the product Ig was obtained in a 52% yield after purification by preparative reverse-phase HPLC and lyophilisation, using the chromatographic conditions previously described for peptides. Re-analysis by analytical reverse-phase HPLC-UV, LC-MS, MS/MS and MALDI-TOF/TOF is in accordance with a homogenous product. The molecular structure and molecular mass of the product of hydrolysis Ig is outlined in Table 1.

Figure 5:
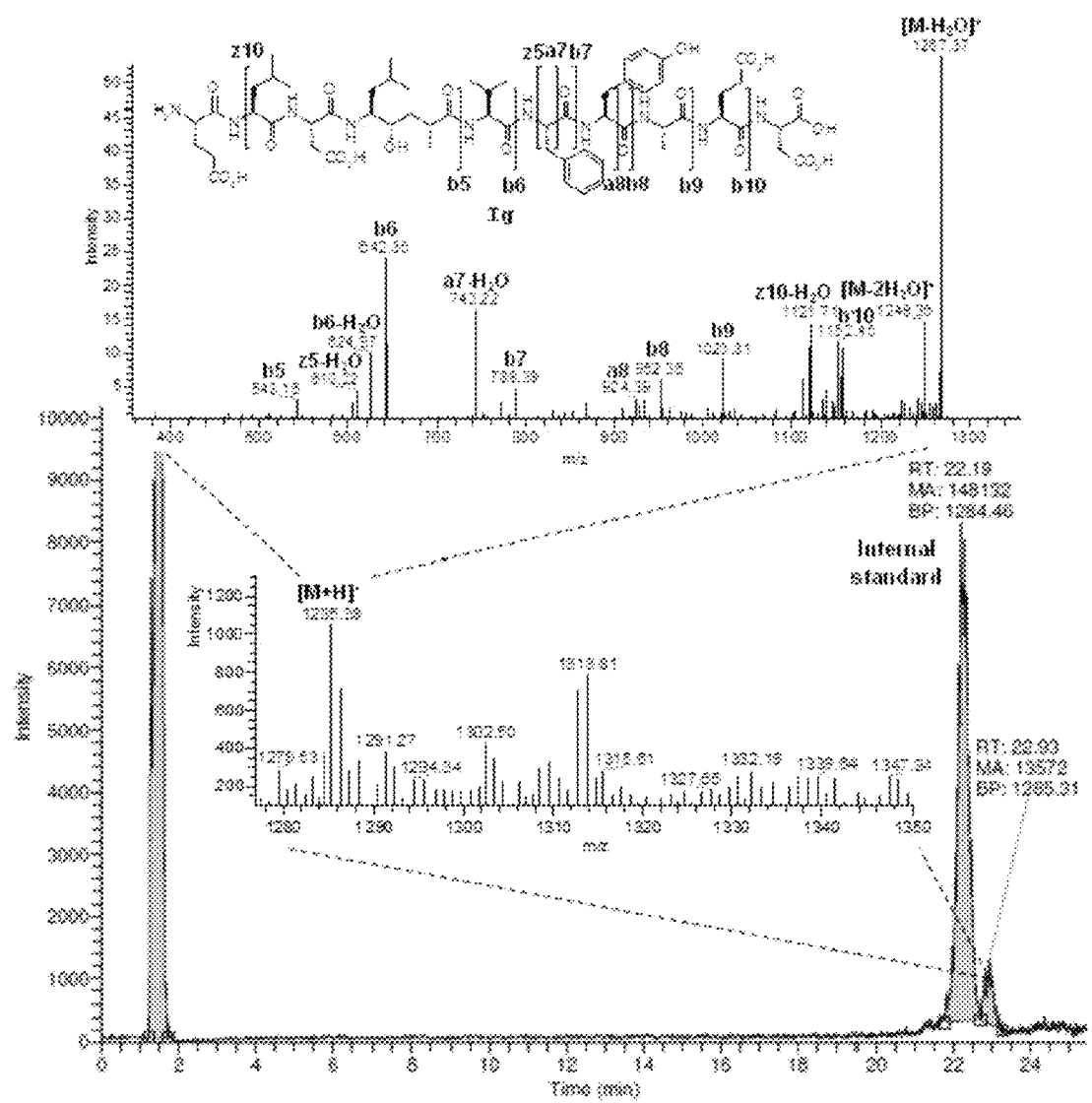
FIG. 5 illustrates the LC-MS chromatogram and Electrospray Ionization Mass Spectrometry (ESI-MS) spectrum of the peak found in the chromatogram at 22.9 min in a brain sample, 1 hour after intravenous administration of Ia in mice; ESI-MS/MS spectrum of the peak 1285.39 amu and identification of the main peaks found according to the expected metabolite, Ig.

An in vivo pharmacokinetic study was performed in order to evaluate the capacity of the best inhibitor in vitro, compound Ia, to reach the brain in mice. Both serum and brain samples were analyzed after intravenous administration of Ia. In serum samples, compound Ia was not detected by HPLC-FLU half an hour after intravenous administration. This indicates that Ia is rapidly distributed, metabolized or eliminated in mice. Accordingly, compound Ia with a peak of 1326.5 amu and a retention time of 23.6 minutes could not be detected in brain samples; however, a metabolite with a peak of 1285.4 amu (FIG. 5) and a very close retention time of 22.9 minutes was detected in brain samples by HPLC-FLU and LC-MS even two hours after administration. The fact that this metabolite doesn't appear in serum samples dismisses any potential contamination of brain samples by the blood.

In order to identify the metabolite and according to the mass found it was hypothesized that it could be compound Ig (HVR-4) (table 1) as the molecular ion found (1285.4 amu) is consistent with the calculated exact mass for Ig $[M+H]+$ (1285.6 amu). The $MS^2$ fragmentation of the molecular ion: 1285.4 amu, afforded the fragmentation spectrum shown in FIG. 5 and the main m/z peaks were assigned based on the expected ions given by mMass software for compound Ig: $M-H_2O$ (expected=1267.6, found=1267.4), $M-2H_2O$ (expected=1249.6, found=1249.4), b10 (expected=1152.5, found=1152.5), z10-$H_2O$ (expected=1121.5, found=1121.7), b9 (expected=1023.5, found=1023.3), b8 (expected=952.4, found=952.4), a8 (expected=924.5, found=924.4), b7 (expected=789.3, found=789.4), a7-$H_2O$ (expected=743.4, found=743.2), b6 (expected=642.4, found=642.4), b6-$H_2O$ (expected=624.4, found=624.3), z5-$H_2O$ (expected=610.2, found=610.2) and b5 (expected=543.3, found=543.2). The correspondence between the observed m/z peaks (FIG. 5) with the expected ions given by mMass suggests compound Ig as the metabolite found in the brain samples.

TABLE 1

Molecular structure and inhibition potency of peptidomimetic BACE-1 inhibitors (mean value ± standard deviation, n = 3).

| # | Structure | M.M./g·mol⁻¹ (exact mass/amu) | $K_{i\ BACE-1}$ / nM | $K_i^{app}$ $_{BACE-2}$ / nM | $K_i^{app}$ $_{BACE-2}$ / $K_{i\ BACE-1}$ |
|---|---|---|---|---|---|
| OM00-3 | 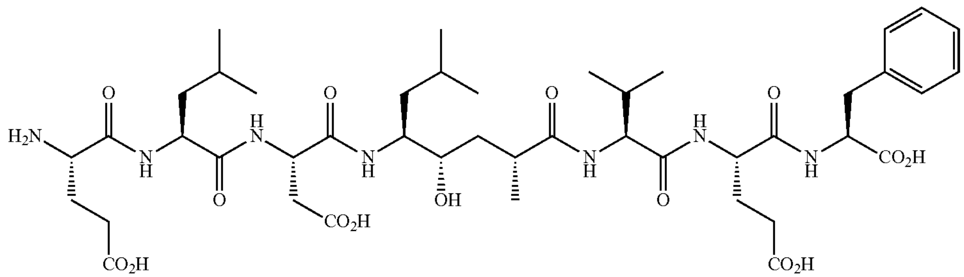 [SMILES: CC(C)C[C@H](NC(=O)[C@@H](N)CCC(=O)O)C(=O)N[C@@H](CC(=O)O)C(=O)N[C@@H](CC(C)C)[C@@H](O)C[C@@H](C)C(=O)N[C@H](C(=O)N[C@@H](CCC(=O)O)C(=O)N[C@@H](Cc1ccccc1)C(=O)O)C(C)C] | 936.1 (935.5) | 1.2 ± 0.4 | 3.0 ± 0.3 | 2.5 |
| Id | 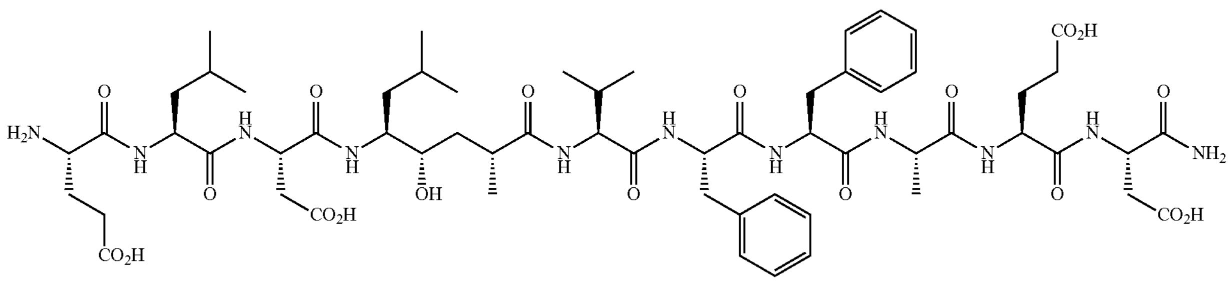 [SMILES: CC(C)C[C@H](NC(=O)[C@@H](N)CCC(=O)O)C(=O)N[C@@H](CC(=O)O)C(=O)N[C@@H](CC(C)C)[C@@H](O)C[C@@H](C)C(=O)N[C@H](C(=O)N[C@@H](Cc1ccccc1)C(=O)N[C@@H](Cc1ccccc1)C(=O)N[C@@H](C)C(=O)N[C@@H](CCC(=O)O)C(=O)N[C@@H](CC(=O)O)C(N)=O)C(C)C] | 1268.4 (1267.6) | 2.0 ± 0.1 | 7.3 ± 0.9 | 3.7 |
| Ic | 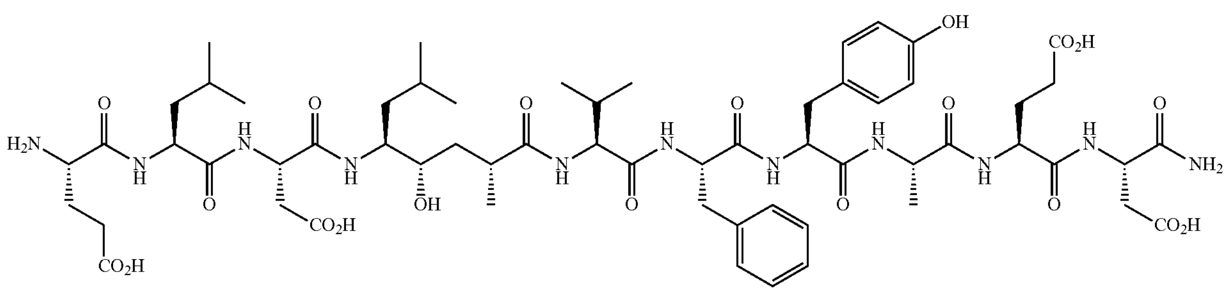 [SMILES: CC(C)C[C@H](NC(=O)[C@@H](N)CCC(=O)O)C(=O)N[C@@H](CC(=O)O)C(=O)N[C@@H](CC(C)C)[C@@H](O)C[C@@H](C)C(=O)N[C@H](C(=O)N[C@@H](Cc1ccccc1)C(=O)N[C@@H](Cc1ccc(O)cc1)C(=O)N[C@@H](C)C(=O)N[C@@H](CCC(=O)O)C(=O)N[C@@H](CC(=O)O)C(N)=O)C(C)C] | 1284.4 (1283.6) | 1.9 ± 0.2 | 14.2 ± 2.2 | 7.5 |

TABLE 1-continued

Molecular structure and inhibition potency of peptidomimetic BACE-1 inhibitors (mean value ± standard deviation, n = 3).

| # | Structure | M.M./g.mol$^{-1}$ (exact mass/amu) | K$_{i\ BACE\text{-}1}$ nM | K$_i^{app}$ BACE-2 nM | K$_i^{app}$ BACE-2 / K$_{i\ BACE\text{-}1}$ |
|---|---|---|---|---|---|
| Ia | 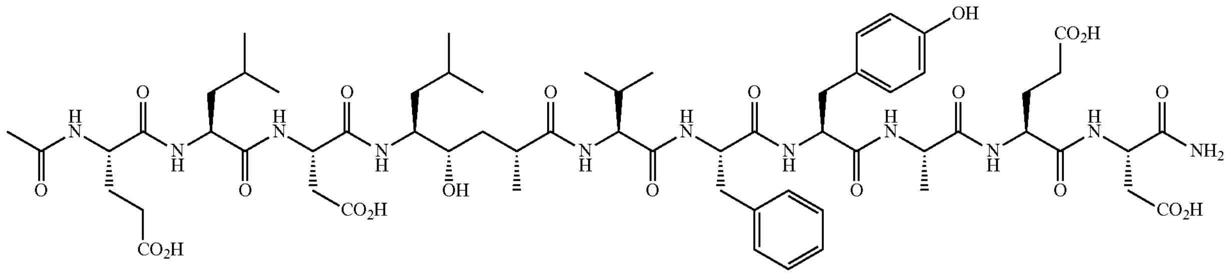 [SMILES: CC(=O)N[C@@H](CCC(=O)O)C(=O)N[C@@H](CC(C)C)C(=O)N[C@@H](CC(=O)O)C(=O)N[C@@H](CC(C)C)[C@@H](O)C[C@@H](C)C(=O)N[C@H](C(=O)N[C@@H](Cc1ccccc1)C(=O)N[C@@H](Cc1ccc(O)cc1)C(=O)N[C@@H](C)C(=O)N[C@@H](CCC(=O)O)C(=O)N[C@@H](CC(=O)O)C(N)=O)C(C)C] | 1326.5 (1325.6) | 2.0 ± 0.6 | 18.3 ± 0.5 | 9.2 |
| Ig | 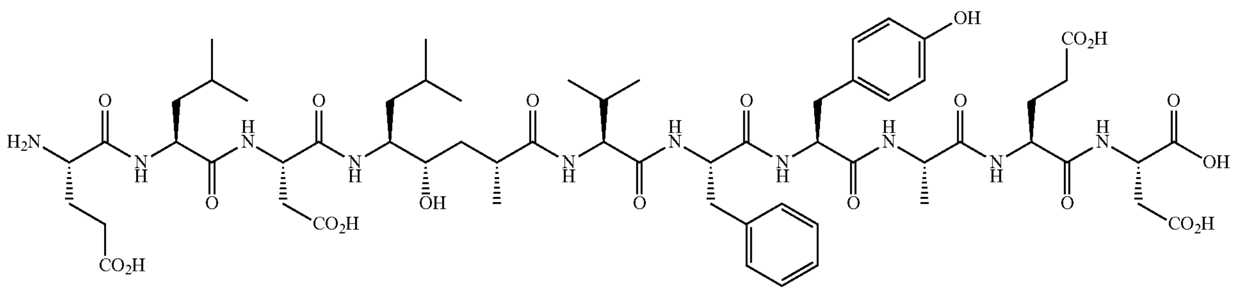 [SMILES: CC(C)C[C@H](NC(=O)[C@@H](N)CCC(=O)O)C(=O)N[C@@H](CC(=O)O)C(=O)N[C@@H](CC(C)C)[C@@H](O)C[C@@H](C)C(=O)N[C@H](C(=O)N[C@@H](Cc1ccccc1)C(=O)N[C@@H](Cc1ccc(O)cc1)C(=O)N[C@@H](C)C(=O)N[C@@H](CCC(=O)O)C(=O)N[C@@H](CC(=O)O)C(=O)O)C(C)C] | 1285.4 (1284.6) | 1.7 ± 0.2 | 12.7 ± 1.9 | 7.5 |

In order to further confirm the chemical structure of the metabolite as Ig, compound Ic was hydrolyzed in order to generate Ig by chemical deamination of the C-terminal. The C-terminal amide of Ic is the only primary amide present making it the most prone to suffer hydrolysis under moderate basic conditions (scheme 3).

Scheme 3

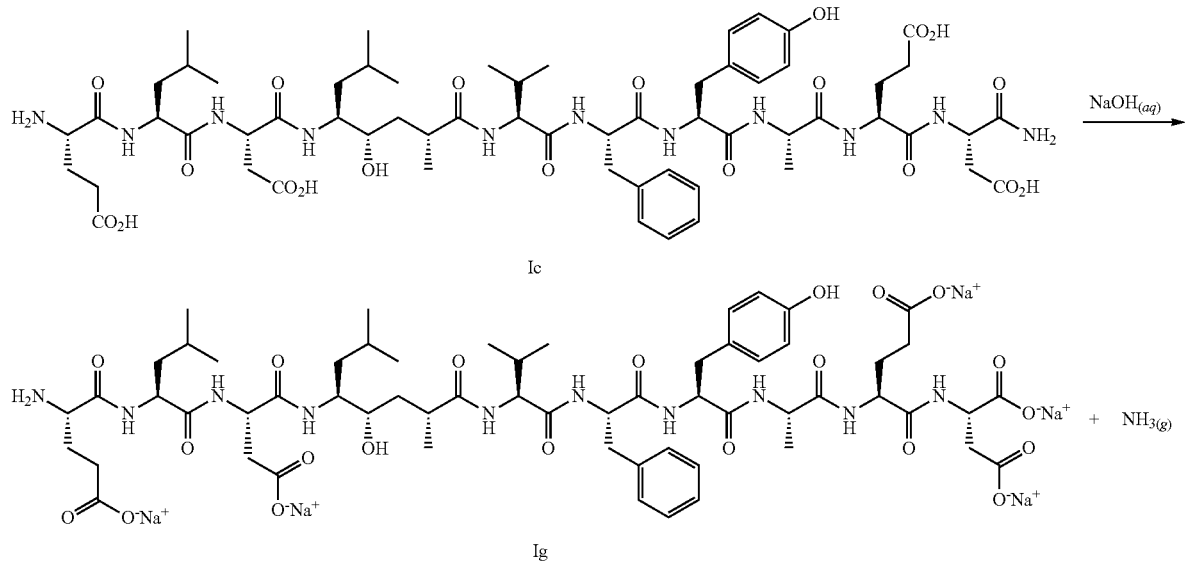

Figure 6:
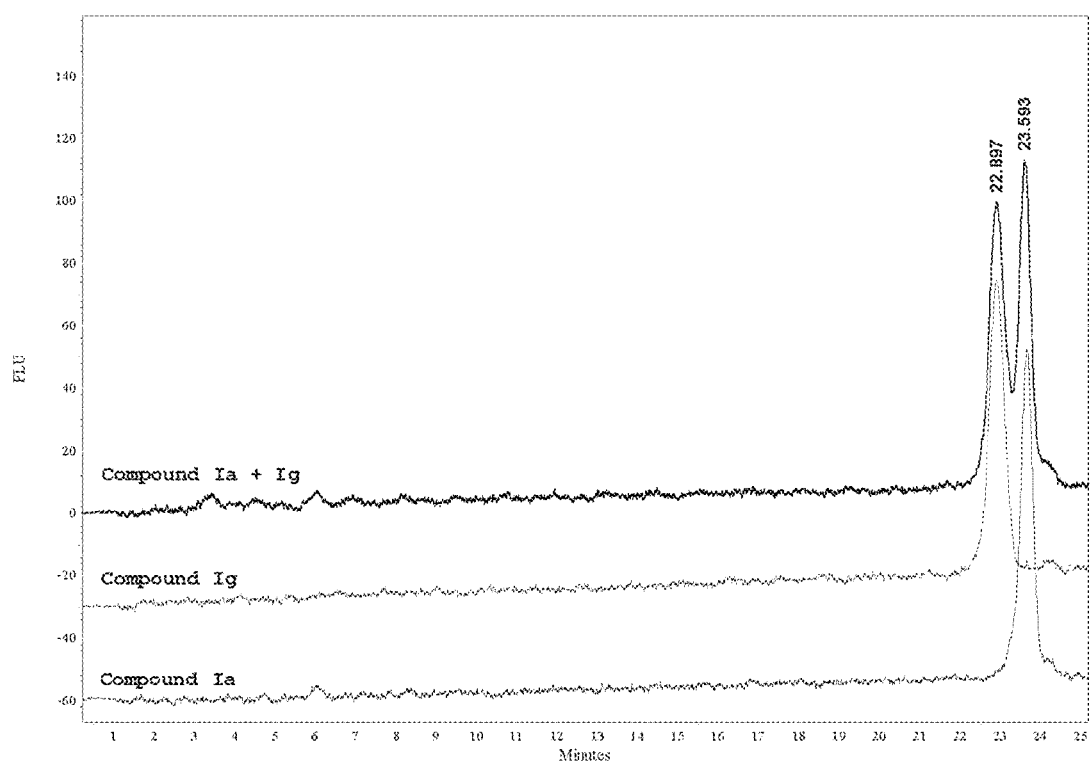
FIG. 6 illustrates the HPLC-FLU chromatograms of Ia, Ig and a mixture of both.
Figure 7:
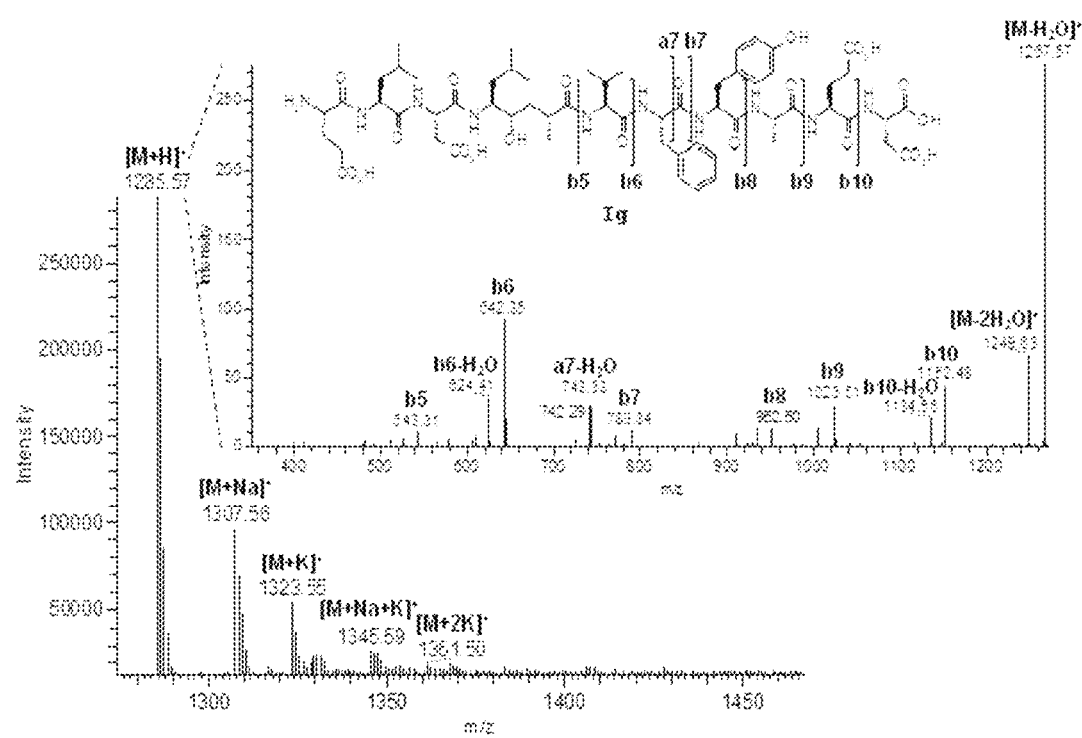
FIG. 7 illustrates the ESI-MS spectrum of the product of basic hydrolysis of Ic (found in the chromatogram at 22.9 min); ESI-MS/MS spectrum of the main peak (1285.57 amu) and identification of the main peaks found according to the expected product, Ig.

The hydrolysis product was analyzed by HPLC-FLU and LC-MS, having the some retention time of 22.9 min (FIG. 6) as the metabolite (FIG. 5) and the major molecular ion found (1285.6 amu) (FIG. 7) is consistent with the calculated exact mass for Ig $[M+H]^+$ (1285.6 amu). A final confirmation of the metabolite structure was provided by the correspondence of the $MS^2$ fragmentation spectrum of the metabolite (FIG. 5) with that of the product of hydrolysis (FIG. 7), where all the main peaks identified in the product of hydrolysis (FIG. 7) were also identified in the fragmentation spectrum of the metabolite, even including peak b10-$H_2O$ (1134.6) not highlighted in FIG. 5 but still present.

In a parallel experiment used to detect Ia by MALDI-TOF/TOF in several brain regions of Wistar rats, Ia also suffered biotransformation into Ig. In agreement with previous experiments in mice, Ia was not detected in the rat cortex after two hours, but Ig was. On the other hand, both Ia and Ig were detected in serum samples of Wistar rats after two hours, raising the hypothesis that disposition of Ia is faster in mice than in Wistar rats.

During the biotransformation of Ia into Ig, the peptide suffered hydrolytic reactions at both the N- and C-terminal amides. Despite being generally considered robust amine derivatives, amides do suffer metabolization. As shown on FIG. 4, Ia is in fact two-fold more stable than Ig in Human serum, possibly because the latter is more susceptible to the attack of serum exopeptidases. On the other hand the opposite happened in mice brain homogenate (FIG. 4), where Ig is more stable than Ia. In the brain the action of amidases acting on terminal amides seem to be more relevant than exopeptidases. Primary amides, such as the C-terminal amide of Ia, are easily converted into the corresponding acid by amidases, which are nonspecific hydrolytic enzymes mainly found in the liver. Amidases may also be found in other organs including kidney and brain, where N-deacylation of acetophenetidines has been observed.

The modifications suffered by Ia when converted to Ig are slight, and resulted in an active metabolite as potent as Ia (1.7±0.2 nM, mean value±standard deviation, n=3, p>0.05, independent two-tailed Student's t-test). The high potency of Ig was expected since it has a very similar structure to Ic (the only difference between Ig and Ic is in the C-terminal, possessing a carboxylic acid instead of an amide) that is as potent as Ia. The benefits of having an amide at the C-terminal is dual, namely the increase in the resistance against metabolization in serum and the absence of a negative charge that could disturb RAGE binding and consequently, BBB crossing. Since Ig was found in the brain, this means that either RAGE binding is not affected or that deamidation is slow enough to allow prior distribution to the brain. Moreover the presence of the carboxylic acid at the C-terminal also didn't affect BACE-1 inhibition due to the long distance in relation to the binding site (FIG. 1).

Looking from a different perspective, the chemical modifications induced by the biotransformation of Ia can be even more important for therapy than the initial compound itself. The primary amine formed at the N-terminal and the carboxylic acid at the C-terminal increase the molecule hydrophilicity, by the generation of a positive and a negative charge, respectively, at physiological pH. These chemical changes will contribute to impede Ig clearance from the CNS into the bloodstream leading to a higher residence time in the CNS since a more hydrophilic molecule will have more difficulty diffusing across the BBB into the bloodstream. This hypothesis gains even more support by the fact that Ig was found at approximately 20 nM in mice brain up to one hour after administration, which is within the therapeutic concentration range, while Ia was not detected after half an hour post administration.

Naturally, the present embodiments and examples are not in any way limited to the embodiments and examples described in this document and a person with average knowledge in the field will be able to predict many possible changes to it without deviating from the main idea, as described in the claims.

Abbreviations

A alanine
Aβ amyloid beta peptide
Aβ (17-23) amyloid beta peptide sequence between residue number seventeen to the twenty third
AD Alzheimer's disease
Ala alanine
APP amyloid precursor protein
APP (272-279) amyloid protein precursor sequence between residue two hundred and seventy two to the residue two hundred and seventy nine
Arg arginine
Asn asparagine
Asp aspartic acid
BAIB bis(acetoxy)iodobenzene
BBB blood brain barrier
Boc tert-butoxycarbonyl
C cysteine
Cys cysteine
D aspartic acid
DCM dichloromethane
DIEA N,N-diisopropylethylamine
DMHA N,O-dimethylhydroxyamine hydrochloride
DMF dimethylformamide
E glutamic acid
EDC 1-ethyl-3-(3-dimethylaminopropyl)carbodiimide
ESI-MS electrospray ionization mass spectrometry
F phenylalanine
Fmoc fluorenylmethyloxycarbonyl
Fmoc-OSu Fmoc-succinimide
G glycine
Gln glutamine
Glu glutamic acid
Gly glycine
H histidine
HBTU N,N,N',N'-Tetramethyl-O-(1H-benzotriazol-1-yl)uronium hexafluorophosphate
His histidine
HPLC high performance liquid chromatography
HOBt 1-hydroxybenzotriazole
I isoleucine
Ile isoleucine
K lysine
L leucine
LDA lithium diisopropylamide
Leu leucine
LiAlH$_4$ lithium aluminium hydride
Lys lysine
M methionine
MBHA 4-methylbenzhydrylamine
Met methionine
N asparagine
NMP N-Methyl-2-pyrrolidone
NMR nuclear magnetic resonance
P proline
Phe phenylalanine
Pro proline
Q glutamine
R arginine
RAGE receptor for advanced glycation end products
S serine
Ser serine
T threonine
TBDMSCl tert-buthyldimethylchlorosilane
tBu tert-butoxy
TEMPO 2,2,6,6-Tetramethylpiperidin-1-yl)oxy
TFA trifluoroacetic acid
THF tetrahydrofuran
Thr threonine
TLC thin layer chromatography
Trp tryptophan
Tyr tyrosine
UV ultra-violet
V valine
Val valine
W tryptophan
Y tyrosine

The invention claimed is:

1. A β-secretase 1 inhibitor compound of the general formula I:

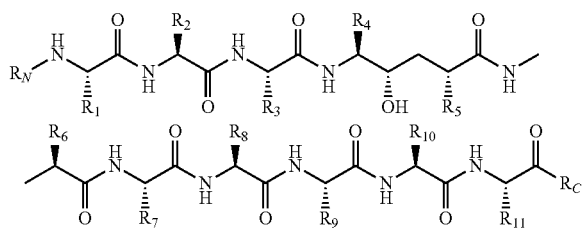

in which:

$R_1$ represents —H, —$CH_2CH_2SCH_3$, —$CH_2CONH_2$, —$CH_2CH_2CONH_2$, —$CH_2COO^-$ or —$CH_2CH_2COO^-$;

$R_2$ represents —$CH(CH_3)_2$, —$CH_2CH(CH_3)_2$, (1S)—$CH(CH_3)CH_2CH_3$, —$CH_2$—(4-(1H-imidazol-3-ium)) or —$CH_2CH_2COO^-$;

$R_3$ represents —$CH_3$, —$CH_2CH(CH_3)_2$, —$CH_2$-phenyl, —$CH_2$-phenol, —$CH_2CH_2SCH_3$, —$CH_2OH$, —$CH_2CONH_2$, —$CH_2COO^-$ or —$CH_2CH_2COO^-$;

$R_4$ represents —$CH_2CH(CH_3)_2$, —$CH_2$-phenyl, —$CH_2$-phenol or —$CH_2CH_2SCH_3$;

$R_5$ represents —$CH_3$;

$R_6$ represents —$CH_3$, —$CH(CH_3)_2$, —$CH_2CH(CH_3)_2$ or (1S)—$CH(CH_3)CH_2CH_3$;

$R_7$ and $R_8$ are independently selected from —$CH_2$-phenyl, —$CH_2$-phenol or —$CH_2$-(3-indole);

$R_9$ represents —H, —$CH_3$, —$CH(CH_3)_2$, —$CH_2CH(CH_3)_2$, (1S)—$CH(CH_3)CH_2CH_3$ or —$CH_2CH_2*CH_2$, wherein the *$CH_2$ is bonded to the adjacent NH to form a five membered heterocycle;

$R_{10}$ and $R_{11}$ are independently selected from —$CH_2COO^-$ or —$CH_2CH_2COO^-$;

$R_N$ represents —H or —$COCH_3$;

$R_C$ represents —$NH_2$ or —OH, and their enantiomers, diastereomers, tautomers, or pharmaceutically acceptable salts, solvates, protonated forms or deprotonated forms thereof.

2. The compounds according to claim 1, wherein the compound is one of Ia to Ip

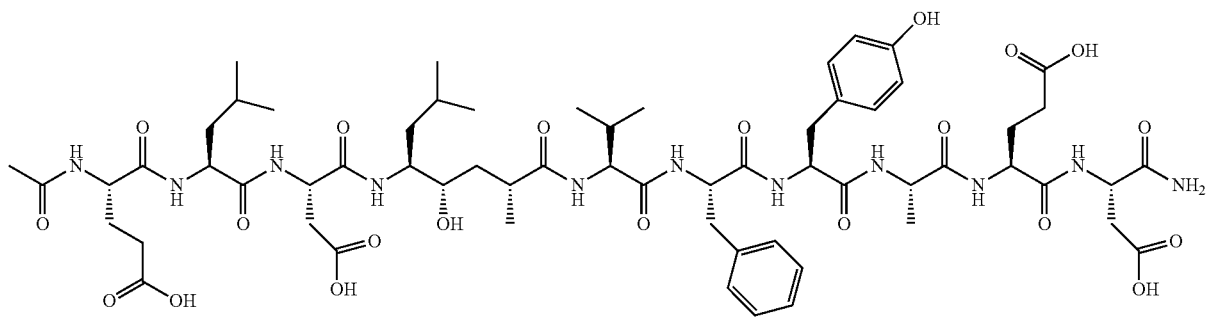

(Ia)

SEQ 1 ELDL AVFYAED

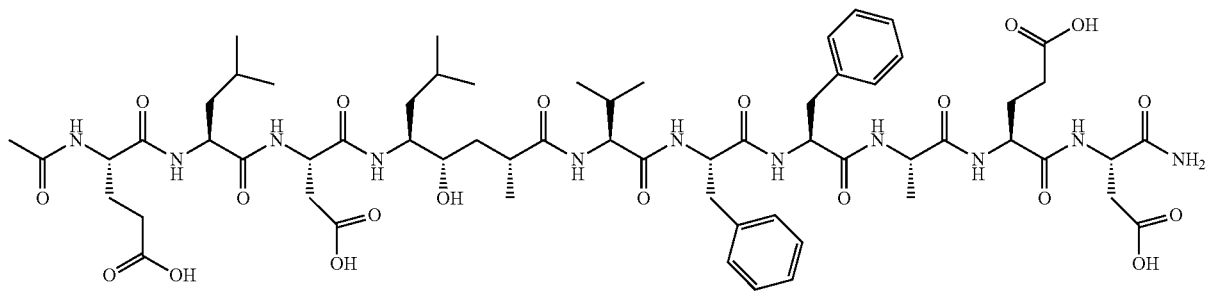

(Ib)

SEQ 2 ELDL AVFFAED (Ic)
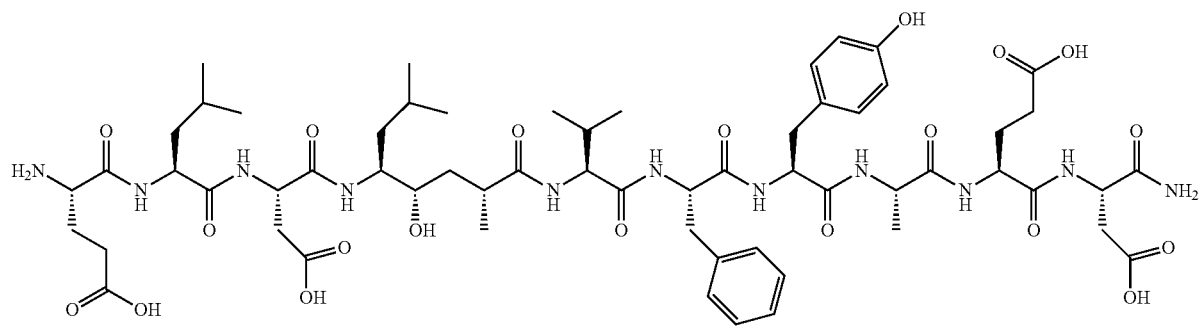
SEQ 1 ELDL AVFYAED
(Id)
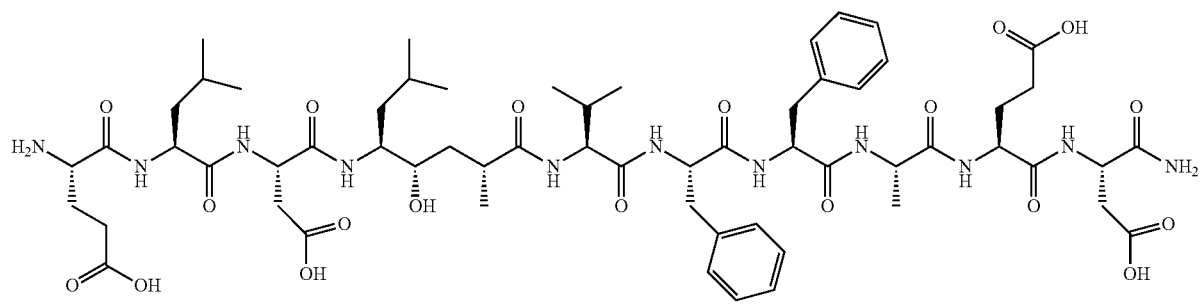
SEQ 2 ELDL AVFFAED
(Ie)
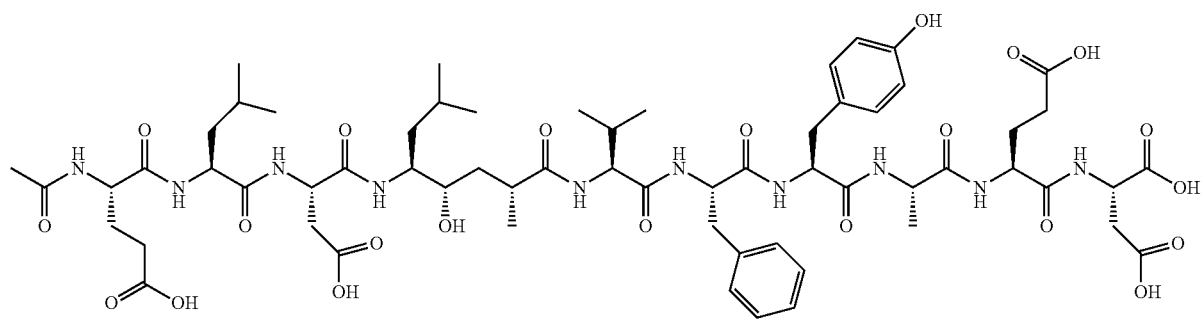
SEQ 1 ELDL AVFYAED
(If)
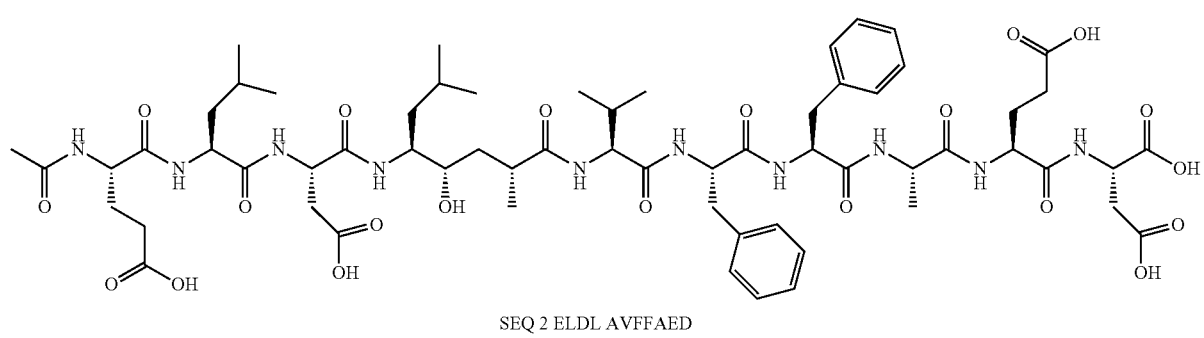
SEQ 2 ELDL AVFFAED (Ig)
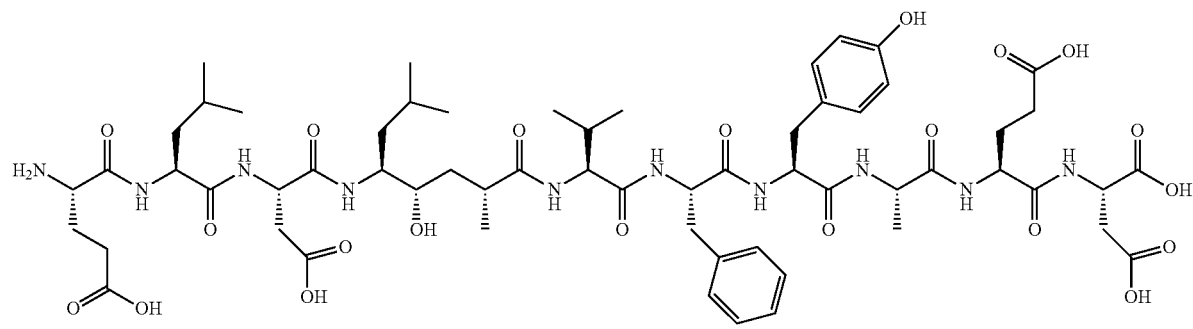
SEQ 1 ELDL AVFYAED
(Ih)
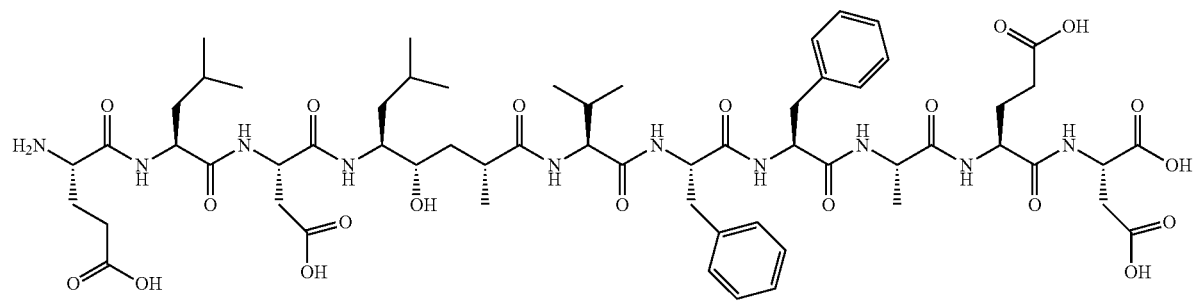
SEQ 2 ELDL AVFFAED
(Ii)
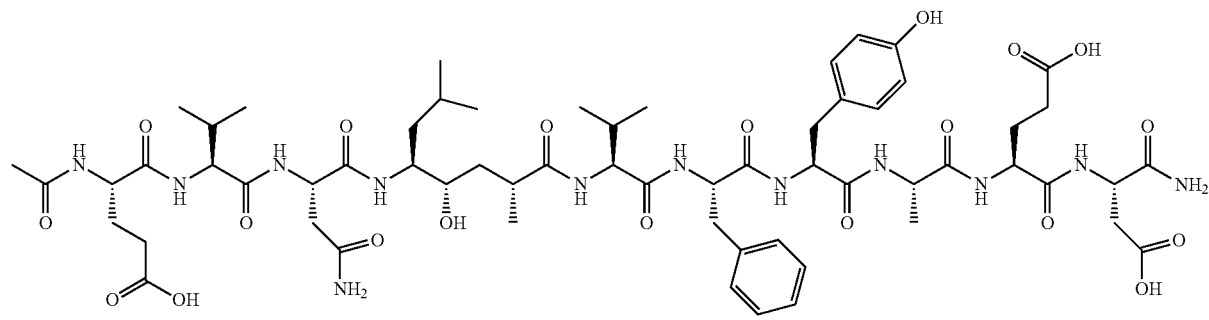
SEQ 3 EVDL AVFYAED
(Ij)
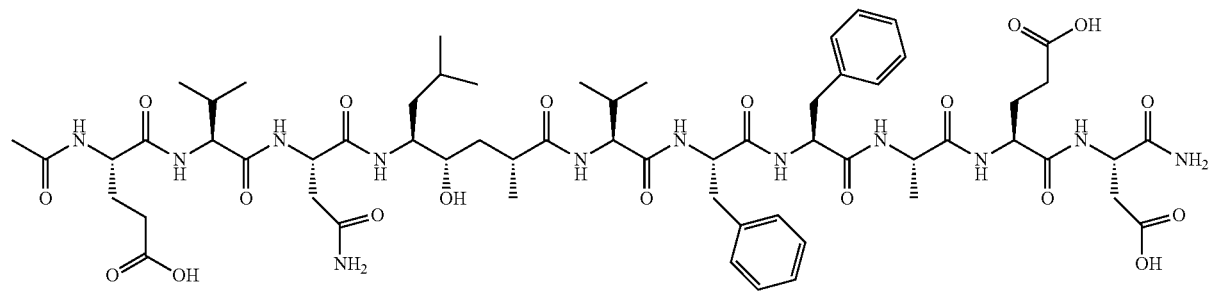
SEQ 4 EVDL AVFFAED

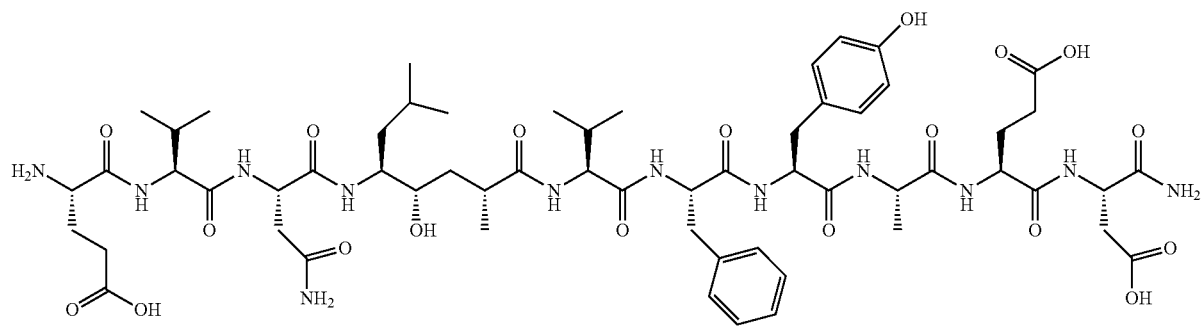
SEQ 3 EVDL AVFYAED
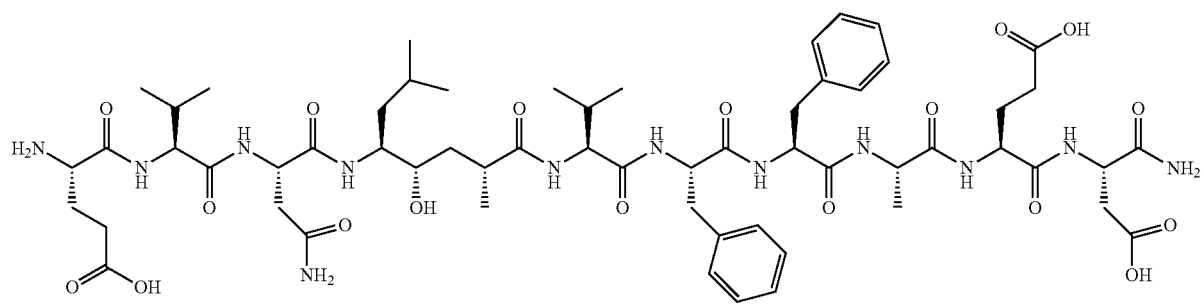
SEQ 4 EVDL AVFFAED
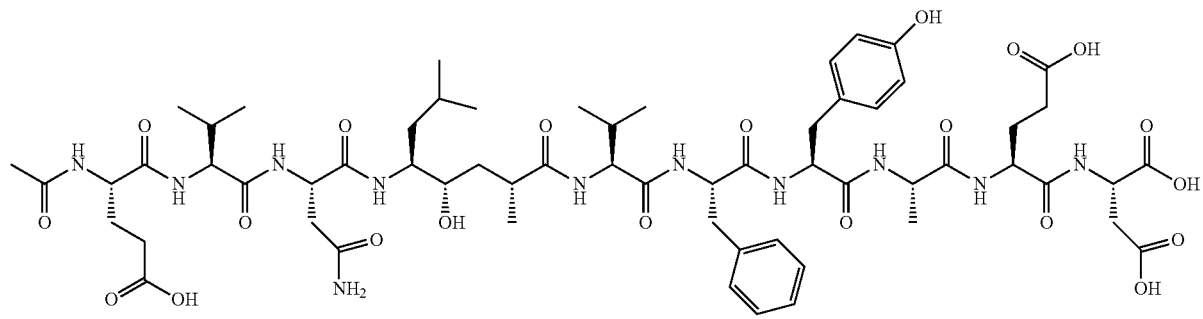
SEQ 3 EVDL AVFYAED
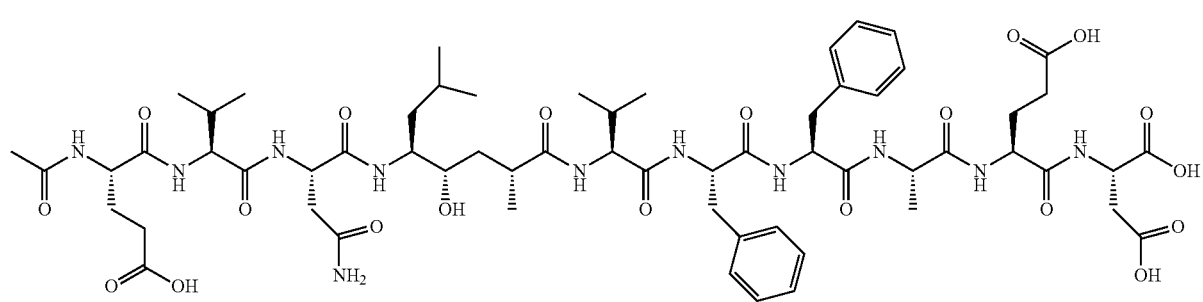
SEQ 4 EVDL AVFFAED

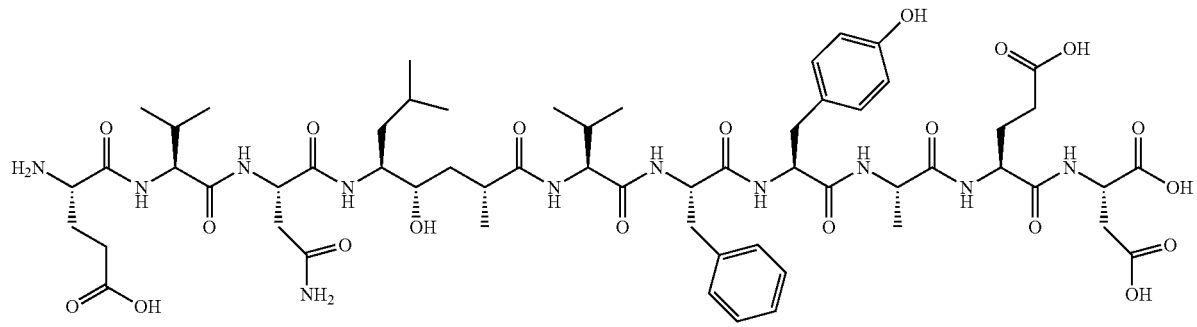

SEQ 3 EVDL AVFYAED

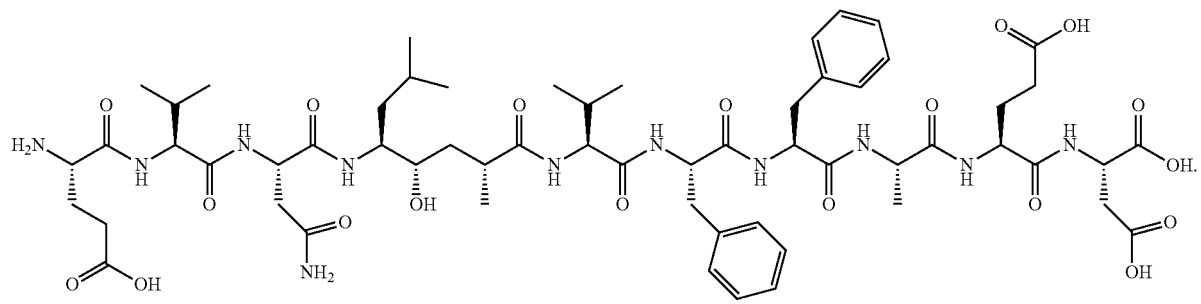

SEQ 4 EVDL AVFFAED

3. Process for the preparation of the compounds described in claim 1, comprising the following steps:
preparing compounds with an amide in the C-terminal by a standard Solid Phase Peptide Synthesis using a Rink amide resin comprising 10 cycles of Fmoc deprotection and amino acids coupling;
or preparing compounds with a carboxylic acid in the C-terminal by a standard Solid Phase Peptide Synthesis using either Fmoc-Asp or Fmoc-Glu, both linked to a Wang resin, comprising at least 9 cycles of Fmoc deprotection and amino acids coupling;
optionally, capping with acetic anhydride, after Fmoc deprotection of the last added amino acid;
and deprotecting the amino acids lateral chains and resin cleavage.

4. The process according to claim 3, wherein each cycle of the solid phase peptide synthesis for the preparation of compounds with an amide in the C-terminal, comprises two Fmoc deprotections, washing, step, a single coupling with HBTU activated amino acid and an additional washing.

5. The process according to the claim 3, wherein each cycle of the solid phase peptide synthesis for the preparation of compounds with a carboxylic acid in the C-terminal, comprises two Fmoc deprotections, washing, step, a single coupling with HBTU activated amino acid and an additional washing.

6. The process according to claim 3, wherein the Fmoc-protected amino acids are sequentially added according to the following cycles:
the first cycle comprises the incorporation of: Fmoc-Asp(OtBu)-OH or Fmoc-Glu(OtBu)-OH;
the second cycle comprises the incorporation of: Fmoc-Asp(OtBu)-OH or Fmoc-Glu(OtBu)-OH;
the third cycle comprises the incorporation of: Fmoc-Gly-OH, Fmoc-Ala-OH, Fmoc-Val-OH, Fmoc-Leu-OH, Fmoc-Ile-OH or Fmoc-Pro-OH;
the fourth cycle comprises the incorporation of: Fmoc-Phe-OH, Fmoc-Tyr(tBu)-OH or Fmoc-Trp(Boc)-OH;
the fifth cycle comprises the incorporation of: Fmoc-Phe-OH, Fmoc-Tyr(tBu)-OH or Fmoc-Trp(Boc)-OH;

the sixth cycle comprises the incorporation of: Fmoc-Ala-OH, Fmoc-Val-OH, Fmoc-Leu-OH or Fmoc-Ile-OH;
the seventh cycle comprises the incorporation of an synthetic Fmoc-dipeptide hydroxyethylene isostere;
the eighth cycle is incorporated: Fmoc-Ala-OH, Fmoc-Leu-OH, Fmoc-Phe-OH, Fmoc-Tyr(tBu)-OH, Fmoc-Met-OH, Fmoc-Ser(tBu)-OH, Fmoc-Asn(Trt)-OH, Fmoc-Asp(OtBu)-OH or Fmoc-Glu(OtBu)-OH;
the ninth cycle comprises the incorporation of: Fmoc-Val-OH, Fmoc-Leu-OH, Fmoc-Ile-OH, Fmoc-His(Trt)-OH or Fmoc-Glu(OtBu)-OH;
and the tenth cycle comprises the incorporation of: Fmoc-Gly-OH, Fmoc-Met-OH, Fmoc-Asn(Trt)-OH, Fmoc-Gln(Trt)-OH, Fmoc-Asp(OtBu)-OH or Fmoc-Glu(OtBu)-OH.

7. The process according to claim 6, wherein the synthetic Fmoc-dipeptide hydroxyethylene isostere is synthesized following the steps:
converting Boc-L-leucine, Boc-L-phenylalanine, Boc-O-2-chlorotrityl-L-tyrosine or Boc-L-methionine into a Weinreb amide by treatment with N,O-dimethylhydroxyamine hydrochloride, 4-methylmorpholine and EDC;
Weinreb amide reducing with LiAlH$_4$, followed by alkylation with lithium benzyl propargyl ether rendering an alkyne;
catalytically hydrogenating the alkyne into a diol;
performing diol selective oxidation with BAIB and TEMPO rendering a lactone;
lactone methylating after treatment with LDA and MeI rendering a methyl-lactone;
opening the methyl-lactone with aqueous lithium hydroxide and selective silylation of the free hydroxyl group with TBDMSCl and imidazole rendering an acid;
and performing acid tert-Butoxycarbonyl exchange by a fluorenylmethyloxycarbonyl protecting group after treatment with trifluoroacetic acid followed by Fmoc-succinimide in the presence of aqueous NaHCO$_3$, rendering a Fmoc-dipeptide hydroxyethylene isostere.

8. The process according to claim 3, wherein the Fmoc-protected amino acids are sequential added according to the following cycles:
the first cycle comprises the incorporation of: Fmoc-Asp(OtBu)-OH or Fmoc-Glu(OtBu)-OH;
the second cycle comprises the incorporation of: Fmoc-Gly-OH, Fmoc-Ala-OH, Fmoc-Val-OH, Fmoc-Leu-OH, Fmoc-Ile-OH or Fmoc-Pro-OH;
the third cycle comprises the incorporation of: Fmoc-Phe-OH, Fmoc-Tyr(tBu)-OH or Fmoc-Trp(Boc)-OH;
the fourth cycle comprises the incorporation of: Fmoc-Phe-OH, Fmoc-Tyr(tBu)-OH or Fmoc-Trp(Boc)-OH;
the fifth cycle comprises the incorporation of: Fmoc-Ala-OH, Fmoc-Val-OH, Fmoc-Leu-OH or Fmoc-Ile-OH;
the sixth cycle comprises the incorporation of an synthetic Fmoc-dipeptide hydroxyethylene isostere;
the seventh cycle comprises the incorporation of: Fmoc-Ala-OH, Fmoc-Leu-OH, Fmoc-Phe-OH, Fmoc-Tyr(tBu)-OH, Fmoc-Met-OH, Fmoc-Ser(tBu)-OH, Fmoc-Asn(Trt)-OH, Fmoc-Asp(OtBu)-OH or Fmoc-Glu(OtBu)-OH;
the eighth cycle comprises the incorporation of: Fmoc-Val-OH, Fmoc-Phe-OH, Fmoc-Ile-OH, Fmoc-His(Trt)-OH or Fmoc-Glu(OtBu)-OH;
and the ninth cycle comprises the incorporation of: Fmoc-Gly-OH, Fmoc-Met-OH, Fmoc-Asn(Trt)-OH, Fmoc-Gln(Trt)-OH, Fmoc-Asp(OtBu)-OH or Fmoc-Glu(OtBu)-OH.

9. The process according to claim 8, wherein the synthetic Fmoc-dipeptide hydroxyethylene isostere is synthesized following, the steps:
converting Boc-L-leucine, Boc-L-phenylalanine, Boc-O-2-chlorotrityl-L-tyrosine or Boc-L-methionine into a Weinreb amide by treatment with N,O-dimethylhydroxyamine hydrochloride, 4-methylmorpholine and EDC;
Weinreb amide reducing with LiAlH$_4$, followed by alkylation with lithium benzyl propargyl ether rendering an alkyne;
catalytically hydrogenating the alkyne into a diol;
performing diol selective oxidation with BAIB and (TEMPO rendering a lactone;
lactone methylating after treatment, with LDA and MeI rendering a methyl-lactone;
opening the methyl-lactone ring with aqueous lithium hydroxide and selective silylation of the free hydroxyl group with TBDMSCl and imidazole rendering an acid;
and performing acid tert-Butoxycarbonyl exchange by a fluorenylmethyloxycarbonyl protecting group after treatment with trifluoroacetic acid followed by Fmoc-succinimide in the presence of aqueous NaHCO$_3$, rendering a Fmoc-dipeptide hydroxyethylene isostere.

10. Medicament comprising one or more compounds described in claim 1 and a pharmaceutically acceptable carrier or diluent.

11. A method for the treatment of neurological disorders or conditions that is selected from the group consisting of Alzheimer's disease, amyotrophic lateral sclerosis, cerebral amyloid angiopathy, cerebral ischemia, dementia, hereditary cerebral haemorrhage with, amyloidosis of the Dutch-type, inclusion body myositis, mild cognitive impairment, Parkinson's disease, and Down's syndrome comprising administering one of the compound according to claim 1 to the mammal in need thereof.

12. Process for the preparation of the compounds described in claim 2, comprising the following steps:
preparing compounds with an amide in the C-terminal by a standard Solid Phase Peptide Synthesis using a Rink amide resin comprising 10 cycles of Fmoc deprotection and amino acids coupling;
or preparing compounds with a carboxylic acid in the C-terminal by a standard Solid Phase Peptide Synthesis using either Fmoc-Asp or Fmoc-Glu, both linked to a Wang resin, comprising at least 9 cycles of Fmoc deprotection and amino acids coupling;
optionally, capping with acetic anhydride, after Fmoc deprotection of the last added amino acid;
and deprotecting the amino acids lateral chains and resin cleavage.

13. The process according to claim 4, wherein the Fmoc-protected amino acids are sequentially added according to the following cycles:
the first cycle comprises the incorporation of: Fmoc-Asp(OtBu)-OH or Fmoc-Glu(OtBu)-OH;
the second cycle comprises the incorporation of: Fmoc-Asp(OtBu)-OH or Fmoc-Glu(OtBu)-OH;
the third cycle comprises the incorporation of: Fmoc-Gly-OH, Fmoc-Ala-OH, Fmoc-Val-OH, Fmoc-Leu-OH, Fmoc-Ile-OH or Fmoc-Pro-OH;
the fourth cycle comprises the incorporation of: Fmoc-Phe-OH, Fmoc-Tyr(tBu)-OH or Fmoc-Trp(Boc)-OH;
the fifth cycle comprises the incorporation of: Fmoc-Phe-OH, Fmoc-Tyr(tBu)-OH or Fmoc-Trp(Boc)-OH;
the sixth cycle comprises the incorporation of: Fmoc-Ala-OH, Fmoc-Val-OH, Fmoc-Leu-OH or Fmoc-Ile-OH;

the seventh cycle comprises the incorporation of an synthetic Fmoc-dipeptide hydroxyethylene isostere;

the eighth cycle is incorporated: Fmoc-Ala-OH, Fmoc-Leu-OH, Fmoc-Phe-OH, Fmoc-Tyr(tBu)-OH, Fmoc-Met-OH, Fmoc-Ser(tBu)-OH, Fmoc-Asn(Trt)-OH, Fmoc-Asp(OtBu)-OH or Fmoc-Glu(OtBu)-OH;

the ninth cycle comprises the incorporation of: Fmoc-Val-OH, Fmoc-Leu-OH, Fmoc-Ile-OH, Fmoc-His(Trt)-OH or Fmoc-Glu(OtBu)-OH;

and the tenth cycle comprises the incorporation of: Fmoc-Gly-OH, Fmoc-Met-OH, Fmoc-Asn(Trt)-OH, Fmoc-Gln(Trt)-OH, Fmoc-Asp(OtBu)-OH or Fmoc-Glu(OtBu)-OH.

14. The process according to claim 5, wherein the Fmoc-protected amino acids are sequential added according to the following cycles:

the first cycle comprises the incorporation of: Fmoc-Asp(OtBu)-OH or Fmoc-Glu(OtBu)-OH;

the second cycle comprises the incorporation of: Fmoc-Gly-OH, Fmoc-Ala-OH, Fmoc-Val-OH, Fmoc-Leu-OH, Fmoc-Ile-OH or Fmoc-Pro-OH;

the third cycle comprises the incorporation of: Fmoc-Phe-OH Fmoc-Tyr(tBu)-OH or Fmoc-Trp(Boc)-OH;

the fourth cycle comprises the incorporation of: Fmoc-Phe-OH, Fmoc-Tyr(tBu)-OH or Fmoc-Trp(Boc)-OH;

the fifth cycle comprises the incorporation of: Fmoc-Ala-OH, Fmoc-Val-OH, Fmoc-Leu-OH or Fmoc-Ile-OH;

the sixth cycle comprises the incorporation of an synthetic Fmoc-dipeptide hydroxyethylene isostere;

the seventh cycle comprises the incorporation of: Fmoc-Ala-OH, Fmoc-Leu-OH, Fmoc-Phe-OH, Fmoc-Tyr(tBu)-OH, Fmoc-Met-OH, Fmoc-Ser(tBu)-OH, Fmoc-Asn(Trt)-OH, Fmoc-Asp(OtBu)-OH or Fmoc-Glu(OtBu)-OH;

the eighth cycle comprises the incorporation of: Fmoc-Val-OH, Fmoc-Leu-OH, Fmoc-Phe-OH, Fmoc-Ile-OH, Fmoc-His(Trt)-OH or Fmoc-Glu(OtBu)-OH;

and the ninth cycle comprises the incorporation of: Fmoc-Gly-OH, Fmoc-Met-OH, Fmoc-Asn(Trt)-OH, Fmoc-Gln(Trt)-OH, Fmoc-Asp(OtBu)-OH or Fmoc-Glu(OtBu)-OH.

15. Medicament comprising one or more compounds described in claim 2 and a pharmaceutically acceptable carrier or diluent.

16. A method for the treatment of neurological disorders or conditions that is selected from the group consisting of Alzheimer's disease, amyotrophic lateral sclerosis, cerebral amyloid angiopathy, cerebral ischemia, dementia, hereditary cerebral haemorrhage with amyloidosis of the Dutch-type, inclusion body myositis, mild cognitive impairment, Parkinson's disease, and Down's syndrome comprising administering one of the compound according to claim 2 to the mammal in need thereof.

17. A β-secretase 1 inhibitor compound of the general formula I:

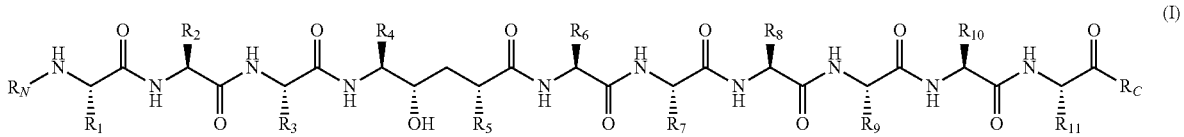

wherein:

$R_1$ represents —$CH_2CH_2SCH_3$, —$CH_2CONH_2$, —$CH_2CH_2CONH_2$, —$CH_2COO^-$ or —$CH_2CH_2COO^-$;

$R_2$ represents —$CH(CH_3)_2$, —$CH_2CH(CH_3)_2$, (1S)—CH($CH_3$)$CH_2CH_3$, —$CH_2$—(4-(1H-imidazol-3-ium)) or —$CH_2CH_2COO^-$;

$R_3$ represents —$CH_3$, —$CH_2CH(CH_3)_2$, —$CH_2$-phenyl, —$CH_2$-phenol, —$CH_2CH_2SCH_3$, $CH_2OH$, —$CH_2CONH_2$, —$CH_2COO^-$ or —$CH_2CH_2COO^-$;

$R_4$ represents —$CH_2CH(CH_3)_2$, —$CH_2$-phenyl, —$CH_2$-phenol or —$CH_2CH_2SCH_3$;

$R_5$ represents —$CH_3$;

$R_6$ represents —$CH_3$, —$CH(CH_3)_2$, —$CH_2CH(CH_3)_2$ or (1S)—CH($CH_3$)$CH_2CH_3$;

$R_7$ is independently —$CH_2$-phenyl, —$CH_2$-phenol, or —$CH_2$-(3-indole);

$R_8$ is independently —$CH_2$-phenyl or —$CH_2$-phenol;

$R_9$ represents —H, —$CH_3$, —$CH(CH_3)_2$, —$CH_2CH(CH_3)_2$, (1S)—CH($CH_3$)$CH_2CH_3$ or —$CH_2CH_2$*$CH_2$, wherein the *$CH_2$ is bonded to the adjacent NH to form a five membered heterocycle;

$R_{10}$ and $R_{11}$ are independently selected from —$CH_2COO^-$ or —$CH_2CH_2COO^-$;

$R_N$ represents —H or —$COCH_3$;

$R_C$ represents —$NH_2$ or —OH, and their enantiomers, diastereomers, tautomers, or pharmaceutically acceptable salts, solvates, protonated forms or deprotonated forms thereof.

* * * * *

SEQUENCE LISTING

<160> NUMBER OF SEQ ID NOS: 2

<210> SEQ ID NO 1
<211> LENGTH: 7
<212> TYPE: PRT
<213> ORGANISM: Homo sapiens

<400> SEQUENCE: 1

Leu Val Phe Phe Ala Glu Asp
1               5

<210> SEQ ID NO 2
<211> LENGTH: 8

```
<212> TYPE: PRT
<213> ORGANISM: Homo sapiens

<400> SEQUENCE: 2

Glu Val Lys Met Asp Ala Glu Phe
1               5
```